(12) United States Patent
Bucciaglia et al.

(10) Patent No.: US 10,765,471 B2
(45) Date of Patent: Sep. 8, 2020

(54) ELECTROSURGICAL SEALER AND DIVIDER

(71) Applicant: Bolder Surgical, LLC, Louisville, CO (US)

(72) Inventors: Joseph D. Bucciaglia, Boulder, CO (US); Dale Schmaltz, Fort Collins, CO (US); Jenifer Kennedy, Boulder, CO (US); Casey Kuchta, Boulder, CO (US); Andrew Christoffersen, Commerce City, CO (US); Christopher Deborski, Denver, CO (US)

(73) Assignee: BOLDER SURGICAL, LLC, Louisville, CO (US)

( * ) Notice: Subject to any disclaimer, the term of this patent is extended or adjusted under 35 U.S.C. 154(b) by 168 days.

(21) Appl. No.: 16/155,966

(22) Filed: Oct. 10, 2018

(65) Prior Publication Data
US 2019/0105100 A1 Apr. 11, 2019

Related U.S. Application Data

(63) Continuation-in-part of application No. 15/487,856, filed on Apr. 14, 2017, now abandoned.
(Continued)

(51) Int. Cl.
*A61B 18/12* (2006.01)
*A61B 18/14* (2006.01)
(Continued)

(52) U.S. Cl.
CPC ........ *A61B 18/1445* (2013.01); *A61B 18/085* (2013.01); *A61B 18/1492* (2013.01);
(Continued)

(58) Field of Classification Search
CPC ...... A61B 18/1445; A61B 2018/00077; A61B 2018/00083; A61B 2018/0063; A61B 2018/1455
See application file for complete search history.

(56) References Cited

U.S. PATENT DOCUMENTS

| 4,815,476 A | 3/1989 | Clossick |
| 5,112,343 A | 5/1992 | Thornton |

(Continued)

FOREIGN PATENT DOCUMENTS

| EP | 0765639 | 4/1997 |
| EP | 1372509 B1 | 3/2005 |

(Continued)

OTHER PUBLICATIONS

Kenichi Yamaguchi, Notice of Reasons for Rejection (translation), Sep. 18, 2019, pp. 9, Japanese Patent Office, Japan.
(Continued)

*Primary Examiner* — Daniel W Fowler
(74) *Attorney, Agent, or Firm* — Schneider IP Law LLC; Laura A. Schneider

(57) ABSTRACT

An electrosurgical instrument has a movable tissue cutting mechanism, a first elongated shaft housing at least a proximal portion of the movable tissue cutting mechanism, and a pair of jaws for clamping tissue. Each jaw of the pair of opposing jaws is rotatable relative to the first elongated shaft, and the movable tissue cutting mechanism is slidable relative to the first elongated shaft. A first link has a distal end rotatably coupled to a proximal one of a pair of non-conductive bushings in the first jaw and a proximal end rotatably coupled to a second elongated shaft, the second elongated shaft interior of and translatable relative the first elongated shaft.

18 Claims, 21 Drawing Sheets

Related U.S. Application Data

(60) Provisional application No. 62/323,030, filed on Apr. 15, 2016.

(51) Int. Cl.
  *A61B 18/08* (2006.01)
  *A61B 18/00* (2006.01)

(52) U.S. Cl.
  CPC ... *A61B 18/1206* (2013.01); *A61B 2018/0063* (2013.01); *A61B 2018/00083* (2013.01); *A61B 2018/00136* (2013.01); *A61B 2018/00601* (2013.01); *A61B 2018/00607* (2013.01); *A61B 2018/00708* (2013.01); *A61B 2018/00875* (2013.01); *A61B 2018/126* (2013.01); *A61B 2018/146* (2013.01); *A61B 2018/1455* (2013.01)

(56) References Cited

U.S. PATENT DOCUMENTS

| | | | |
|---|---|---|---|
| 5,197,964 A | 3/1993 | Parins | |
| 5,293,878 A | 3/1994 | Bales et al. | |
| 5,395,364 A | 3/1995 | Anderhub et al. | |
| 5,470,308 A | 11/1995 | Edwards et al. | |
| 5,482,054 A | 1/1996 | Slater et al. | |
| 5,573,535 A | 11/1996 | Viklund | |
| 5,735,849 A | 4/1998 | Baden | |
| 5,891,142 A | 4/1999 | Eggers | |
| 5,947,996 A | 9/1999 | Logeman | |
| 6,024,744 A | 2/2000 | Kese et al. | |
| 6,086,586 A | 7/2000 | Hooven | |
| 6,099,550 A | 8/2000 | Yoon | |
| 6,273,860 B1 | 8/2001 | Kostylev et al. | |
| 7,052,496 B2* | 5/2006 | Yamauchi ......... A61B 18/1442 606/49 | |
| D525,361 S | 7/2006 | Hushka | |
| 7,083,618 B2 | 8/2006 | Couture et al. | |
| 7,090,673 B2 | 8/2006 | Dycus et al. | |
| 7,101,371 B2 | 9/2006 | Dycus et al. | |
| 7,131,971 B2 | 11/2006 | Dycus et al. | |
| 7,156,846 B2 | 1/2007 | Dycus et al. | |
| 7,204,835 B2 | 4/2007 | Latterell et al. | |
| D545,432 S | 6/2007 | Watanabe | |
| 7,255,697 B2 | 8/2007 | Dycus et al. | |
| 7,384,420 B2 | 6/2008 | Dycus et al. | |
| D575,395 S | 8/2008 | Hushka | |
| 7,473,253 B2 | 1/2009 | Dycus et al. | |
| D590,944 S | 4/2009 | Watanabe | |
| 7,588,566 B2 | 9/2009 | Treat et al. | |
| 7,722,607 B2 | 5/2010 | Dumbauld et al. | |
| 7,744,615 B2 | 6/2010 | Couture | |
| 7,766,910 B2 | 8/2010 | Hixson et al. | |
| D634,427 S | 3/2011 | Nishimura | |
| 7,951,165 B2 | 5/2011 | Golden et al. | |
| D657,871 S | 4/2012 | Hesseling | |
| 8,241,284 B2 | 4/2012 | Dycus et al. | |
| 8,197,479 B2 | 6/2012 | Olson et al. | |
| 8,241,282 B2 | 8/2012 | Unger et al. | |
| 8,267,936 B2 | 9/2012 | Hushka et al. | |
| 8,394,094 B2 | 3/2013 | Edwards et al. | |
| 8,439,911 B2 | 5/2013 | Mueller | |
| 8,540,711 B2 | 9/2013 | Dycus et al. | |
| 8,591,510 B2 | 11/2013 | Allen et al. | |
| 8,617,187 B2 | 12/2013 | Hamilton et al. | |
| 8,647,341 B2 | 2/2014 | Dycus et al. | |
| 8,939,975 B2 | 1/2015 | Twomey et al. | |
| D728,786 S | 5/2015 | Hart et al. | |
| 9,033,981 B2 | 5/2015 | Olson et al. | |
| 9,039,694 B2 | 5/2015 | Ross et al. | |
| 9,055,961 B2 | 6/2015 | Manzo et al. | |
| 9,113,907 B2 | 8/2015 | Allen et al. | |
| 9,113,941 B2 | 8/2015 | Kappus et al. | |
| 9,144,455 B2 | 9/2015 | Kennedy et al. | |
| 9,232,974 B2 | 1/2016 | Dycus et al. | |
| 9,241,759 B2 | 1/2016 | Dycus et al. | |
| D758,581 S | 6/2016 | Michelini et al. | |
| 9,381,059 B2 | 7/2016 | Garrison | |
| 9,492,225 B2 | 11/2016 | Dycus et al. | |
| 9,510,827 B2 | 12/2016 | Kostrzewski | |
| 9,510,906 B2 | 12/2016 | Boudreaux et al. | |
| 9,539,054 B2 | 1/2017 | Peterson et al. | |
| D779,668 S | 2/2017 | Michelini et al. | |
| 9,636,169 B2 | 5/2017 | Allen et al. | |
| 9,655,675 B2 | 5/2017 | Olson et al. | |
| 9,737,357 B2 | 8/2017 | Dycus et al. | |
| 9,820,765 B2 | 11/2017 | Allen et al. | |
| 9,861,378 B2 | 1/2018 | Allen et al. | |
| 9,861,430 B2 | 1/2018 | Dycus et al. | |
| 9,901,390 B2 | 2/2018 | Allen et al. | |
| 9,949,787 B2 | 4/2018 | Dycus et al. | |
| 9,955,858 B2 | 5/2018 | Pamnani et al. | |
| 9,956,030 B2 | 5/2018 | Allen et al. | |
| 9,974,605 B2 | 5/2018 | Garrison et al. | |
| 9,987,076 B2 | 6/2018 | Kappus et al. | |
| 10,058,376 B2 | 8/2018 | Horner et al. | |
| 10,085,794 B2 | 10/2018 | Kerr et al. | |
| 10,098,689 B2 | 10/2018 | Soni | |
| 10,154,877 B2 | 12/2018 | Schechter et al. | |
| 10,188,451 B2 | 1/2019 | Peterson et al. | |
| 10,231,776 B2 | 3/2019 | Artale | |
| 10,251,696 B2 | 4/2019 | Dycus et al. | |
| 10,258,404 B2 | 4/2019 | Wang et al. | |
| 10,265,121 B2 | 4/2019 | Dycus et al. | |
| RE47,375 E | 5/2019 | Shields et al. | |
| 10,278,769 B2 | 5/2019 | Mueller et al. | |
| 10,278,772 B2 | 5/2019 | Peterson et al. | |
| 10,307,203 B2 | 6/2019 | Wyatt et al. | |
| 10,335,227 B2 | 7/2019 | Heard | |
| 10,368,939 B2 | 8/2019 | Sartor et al. | |
| 10,413,352 B2 | 9/2019 | Thomas et al. | |
| 10,441,351 B2 | 10/2019 | Garrison | |
| 10,568,682 B2 | 2/2020 | Dycus et al. | |
| 10,595,932 B2 | 3/2020 | Twomey et al. | |
| 2002/0107517 A1 | 8/2002 | Witt et al. | |
| 2009/0171354 A1* | 7/2009 | Deville ............. A61B 18/1445 606/51 | |
| 2017/0049445 A1 | 2/2017 | Kostrzewski | |
| 2017/0119459 A1 | 5/2017 | Schechter et al. | |
| 2017/0238991 A1 | 8/2017 | Worrell et al. | |
| 2017/0296258 A1 | 10/2017 | Bucciaglia et al. | |
| 2018/0049763 A1 | 2/2018 | Kappus et al. | |
| 2018/0132883 A1 | 5/2018 | Asher et al. | |

FOREIGN PATENT DOCUMENTS

| | | |
|---|---|---|
| EP | 1681027 B1 | 12/2008 |
| EP | 1535581 B1 | 7/2010 |
| EP | 1628586 B1 | 7/2011 |
| EP | 2272454 B1 | 2/2012 |
| EP | 2275049 B1 | 10/2013 |
| EP | 2382938 B1 | 9/2014 |
| EP | 1594755 B1 | 6/2015 |
| EP | 2382936 B1 | 6/2015 |
| EP | 2294998 B1 | 7/2015 |
| EP | 2246003 B1 | 12/2015 |
| EP | 2428177 B1 | 7/2016 |
| EP | 2668922 B1 | 10/2016 |
| EP | 2664294 B1 | 12/2016 |
| EP | 2675383 B1 | 7/2017 |
| EP | 2489318 B1 | 9/2017 |
| EP | 3210557 B1 | 10/2018 |
| EP | 3165189 B1 | 11/2019 |
| WO | 97/43967 | 11/1997 |
| WO | 02080783 A1 | 10/2002 |
| WO | 2009/070780 A1 | 6/2009 |
| WO | 2011/097469 A2 | 8/2011 |
| WO | 2011/156310 A1 | 12/2011 |

(56) References Cited

FOREIGN PATENT DOCUMENTS

WO     2012/044606 A2    4/2012
WO     2015/081042 A1    6/2015

OTHER PUBLICATIONS

Seiwa Patent & Law, Amendment in Response to Office Action in Corresponding Japanese Patent Application No. 2018-553434, dated Feb. 19, 2020, 3 pages, Japan. Translation unavailable.

Seiwa Patent & Law, Argument Accompanying Amendment in Response to Office Action in Corresponding Japanese Patent Application No. 2018-553434, dated Feb. 19, 2020, 4 pages, Japan. Translation unavailable.

Seiwa Patent & Law, Claims as Filed in Amendment in Response to Office Action in Corresponding Japanese Patent Application No. 2018-553434, dated Feb. 19, 2020, 4 pages, Japan. Translation.

Laura A. Schneider, Concise Explanation of Amendment and Argument Accompanying Amendment in Response to Office Action in Corresponding Japanese Patent Application No. 2018-553434, dated Mar. 16, 2020, 2 pages. Westminster, Colorado.

Japanese Patent Office, Notice of Intention to Grant Claims Filed on Feb. 19, 2020 in Corresponding Japanese Patent Application No. 2018-553434, dated Mar. 10, 2020, 2 pages, Japan. Translation unavailable.

\* cited by examiner

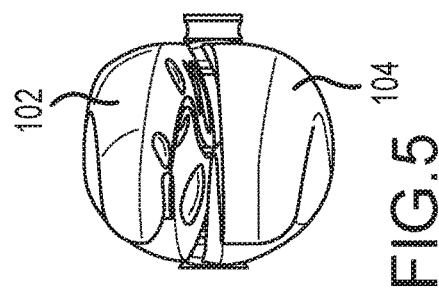
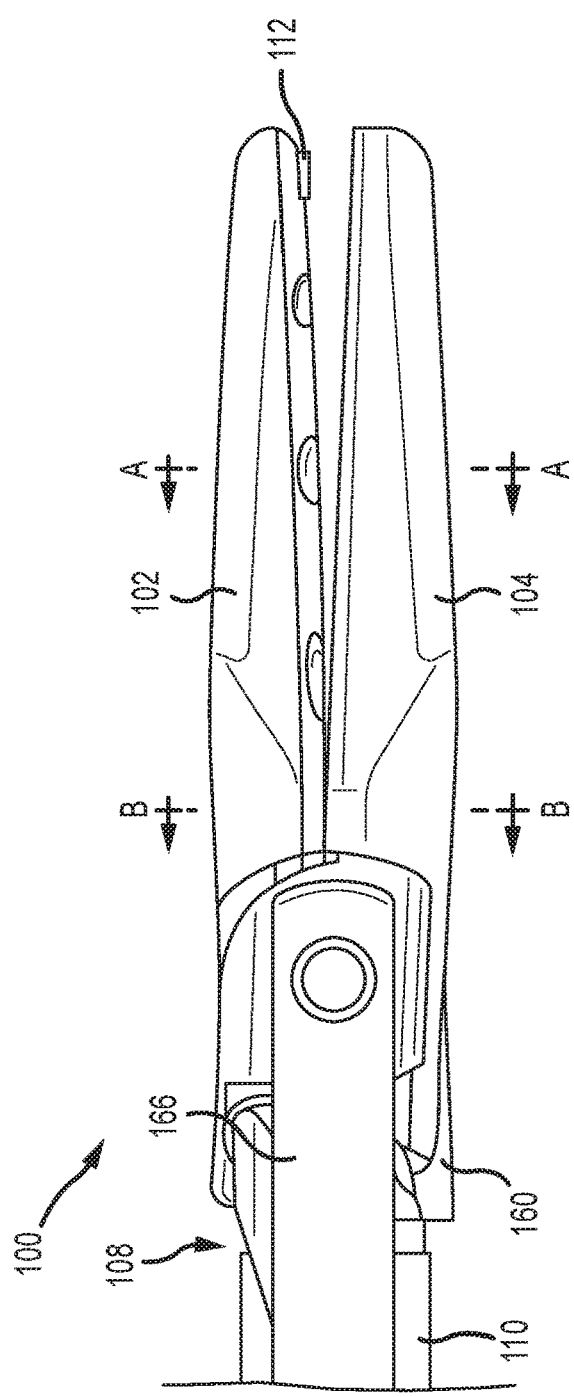
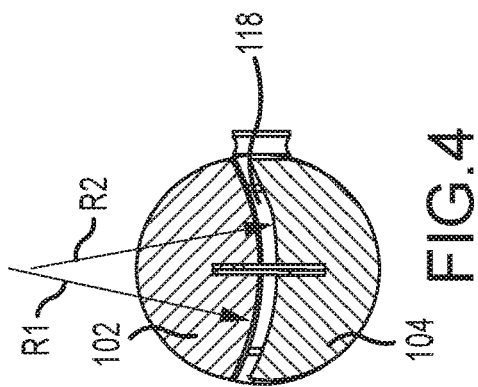
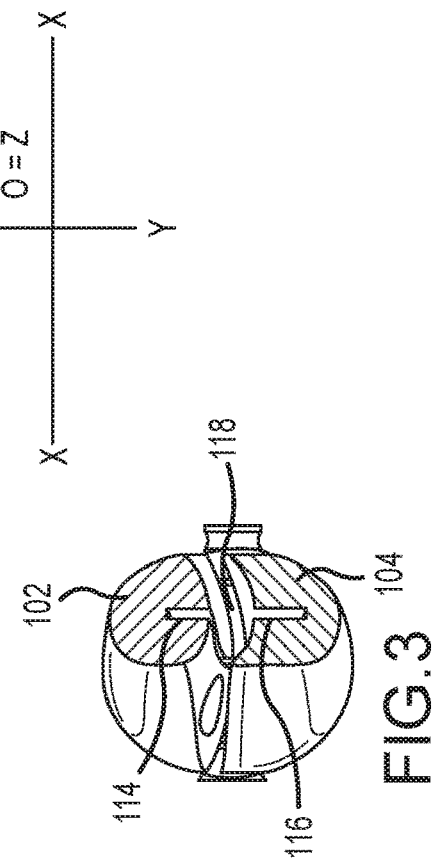

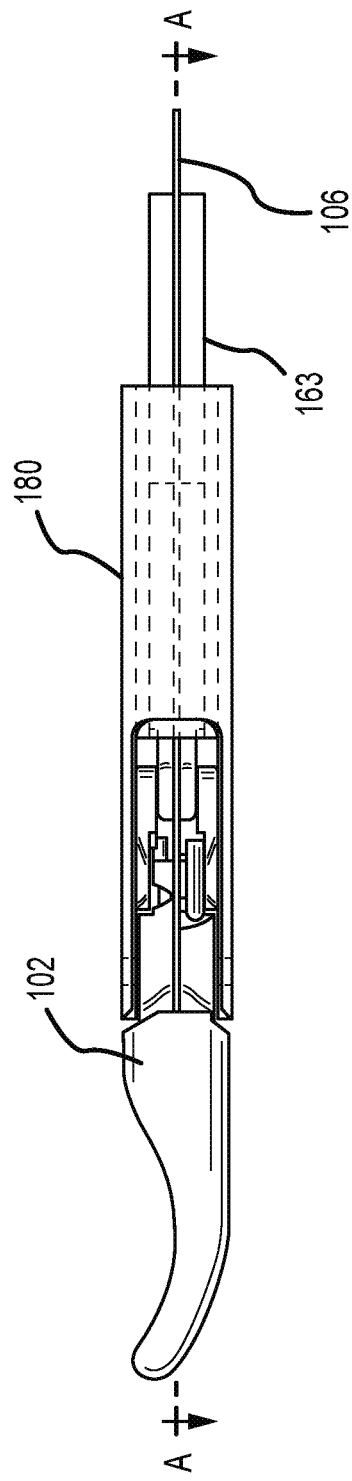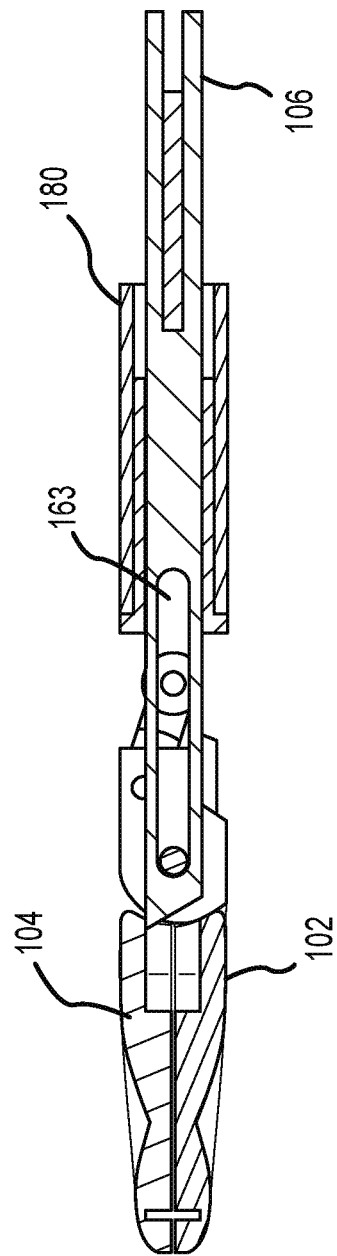
FIG. 13A
SECTION A-A
FIG. 13B

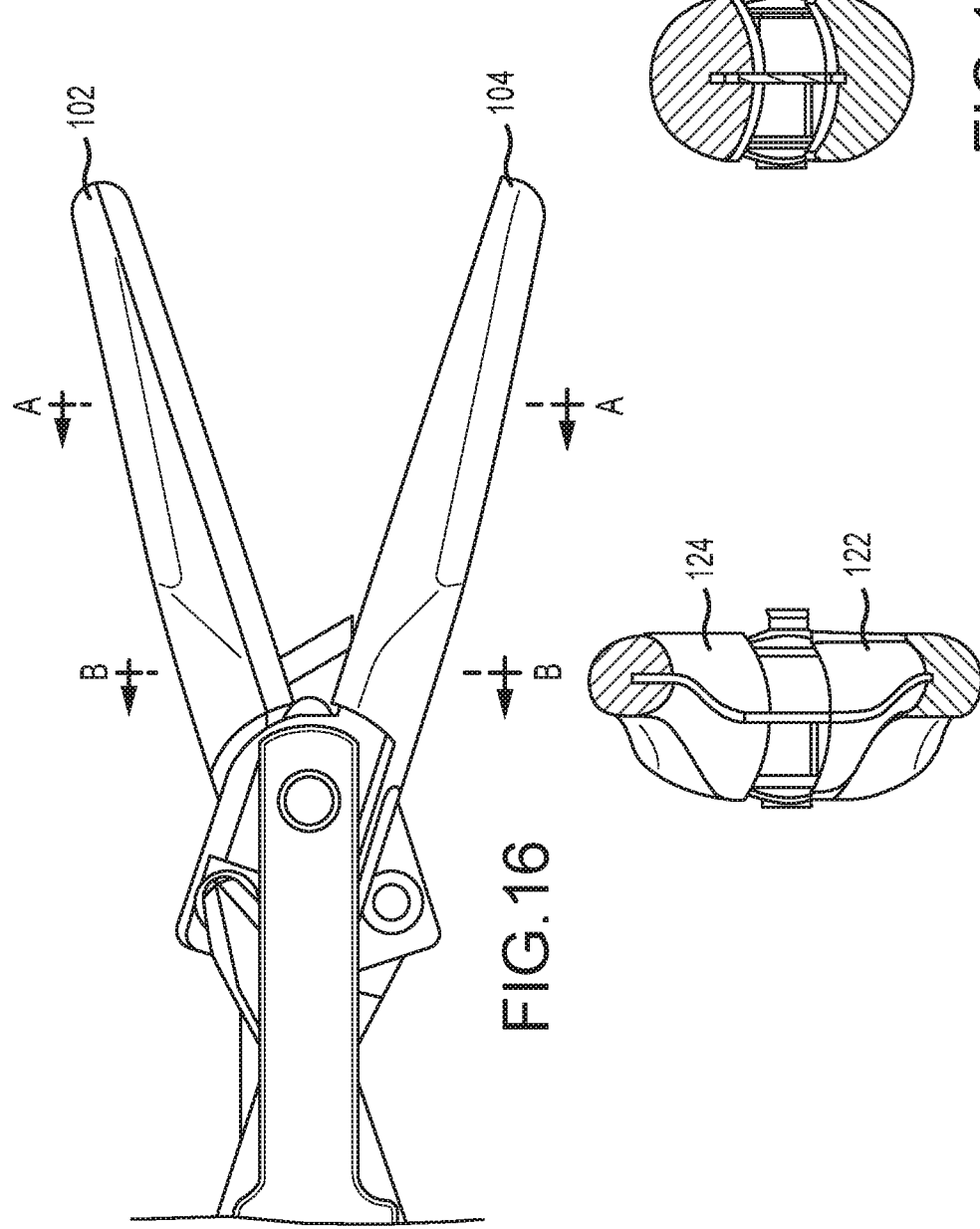

| Seal ID | Tissue Type | Tissue Size | Seal Time (sec) | Max Current (Amps) | Max Voltage (Volts) | Max Power (Watts) | Total Energy (Joules) |
|---|---|---|---|---|---|---|---|
| Seal 1 | Small intestine mesentery | Full jaw with 4 arteries and mesentery | 4 | 2.04 | 96 | 44.8 | 128.55 |
| Seal 2 | Small intestine mesentery | Full jaw - Highly vascularized | 6.04 | 2.48 | 96 | 44.8 | 201.51 |
| Seal 3 | Small intestine mesentery | Full jaw with 4 arteries and mesentery | 7.22 | 2.53 | 96 | 44.8 | 266.05 |
| Seal 4 | Renal artery | 6 mm wide vessel | 4.7 | 2.48 | 96 | 50.4 | 165.6 |
| Seal 5 | Aorta | 15 mm wide vessel | 3.91 | 2.44 | 96 | 45.6 | 139.83 |

Table 1

ELECTROSURGICAL SEALER AND DIVIDER

CROSS-REFERENCE TO RELATED APPLICATIONS

This application is a continuation-in-part of and claims priority to U.S. Utility application Ser. No. 15/487,856 filed on Apr. 14, 2017 and entitled "ELECTROSURGICAL SEALER AND DIVIDER," which claims priority to U.S. Provisional Application No. 62/323,030 filed on Apr. 15, 2016 and entitled "ELECTROSURGICAL SEALER AND DIVIDER." The entire disclosures of these priority documents are hereby incorporated by reference for all proper purposes.

FIELD OF THE INVENTION

This invention is related to medical devices. Specifically, but not intended to limit the invention, embodiments of the invention are related to an electrosurgical instrument for cutting and sealing tissue.

BACKGROUND OF THE INVENTION

A number of electrosurgical devices for cutting and sealing tissue are known in the field.

For example, the currently-available devices include the LigaSure (Ligasure is a trademark brand of Medtronic) line of devices, which includes a combined sealer and divider. This tool provides a pair of jaws that have substantially flat interfaces. That is, as illustrated in FIG. 1, the end effectors have respective sealing surfaces that are substantially flat or in a horizontal plane, and a cutting path that is substantially straight. TheLigaSure tool also provides non-conductive travel stops to prevent the tool from closing completely. The LigaSure tool is known to apply a cycling power that has a sealing power of between 180 Watts and 300 Watts to tissue to cause the tissue to seal, and the tool is prone to cause tissue to stick between the end effectors in use.

The LigaSure tool and other known devices also have electrode surfaces with a large tissue sealing surface.

There remains a need for a device that provides the ability to reliably cut and seal tissue without damaging non-targeted tissue, and/or other new and innovative features.

SUMMARY OF THE INVENTION

An exemplary electrosurgical instrument has a movable tissue cutting mechanism with an elongated slot therethrough. The instrument has a first elongated shaft housing at least a proximal portion of the movable tissue cutting mechanism. The instrument has a pair of opposing jaws having a first jaw and a second jaw, the pair of opposing jaws shaped and configured to move between a closed position for clamping and sealing tissue therebetween and an open position, each one of the pair of opposing jaws having an electrically conductive core member, an elongated slot for receiving the movable tissue cutting mechanism, and a sealing surface having a sealing surface area. The first jaw has a first pair of non-conductive bushings, and the second jaw has a second pair of non-conductive bushings. A pin is coupled to the first elongated shaft and extends through the elongated slot of the movable tissue cutting mechanism and a distal one of the pair of non-conductive bushings in each of the jaws. Each one of the pair of opposing jaws is rotatable relative to the first elongated shaft. The movable tissue cutting mechanism is slidable relative to the first elongated shaft. A first link has a distal end rotatably coupled to a proximal one of the pair of non-conductive bushings in the first jaw and a proximal end rotatably coupled to a second elongated shaft. The second elongated shaft is interior of and translatable relative the first elongated shaft.

BRIEF DESCRIPTION ON THE DRAWINGS

Various objects and advantages and a more complete understanding of the present invention are apparent and more readily appreciated by reference to the following Detailed Description and to the appended claims when taken in conjunction with the accompanying Drawings, where like or similar elements are designated with identical reference numerals throughout the several views and wherein:

FIG. 1 is a perspective view of a prior art device;
FIG. 2 is a side view of a distal portion of a surgical instrument;
FIG. 3 is a cross section view of the instrument in FIG. 2;
FIG. 4 is another cross section view of the instrument in FIG. 2;
FIG. 5 is an end view of the instrument in FIG. 2;
FIG. 6 is a perspective view of a lower jaw and other features of the instrument in FIG. 2;
FIG. 7 is a perspective view of an upper jaw and other features of the instrument in FIG. 2;
FIG. 8 is a lower perspective view of the instrument in FIG. 2 in an open configuration;
FIG. 9 is a lower perspective view of the instrument in FIG. 2 in a closed configuration;
FIG. 9A is a lower perspective view of the instrument in FIG. 9 with a modified feature;
FIG. 10 is a side view of the instrument in FIG. 2 in a closing position;
FIG. 11 is a schematic view illustrating details of the instrument in FIG. 2;
FIG. 12 is a perspective partial transparent view of an exemplary instrument;
FIG. 13A is a top partial transparent view of an exemplary instrument;
FIG. 13B is a side section view of an exemplary instrument;
FIG. 14 is a perspective view of overmolding suitable in an exemplary instrument;
FIG. 15 is a flowchart of an exemplary method;
FIG. 16 is a side view of an exemplary instrument;
FIG. 17 is a distal end view of the instrument in FIG. 16;
FIG. 18 is a section end view of the instrument in FIG. 16;
FIG. 19 is a section end view of the instrument in FIG. 16;
FIG. 20 is a perspective view of an exemplary instrument;
FIG. 21 is an exploded perspective view of an exemplary instrument jaw;
FIG. 22 is a perspective view of the jaw in FIG. 21;
FIG. 23 is a perspective view of an exemplary instrument jaw;
FIG. 24 is a side view of the jaw in FIG. 23;
FIG. 25 is a perspective view of an exemplary surgical instrument;
FIG. 25A is a perspective view of a detail of the instrument in FIG. 25;
FIG. 26 is another perspective view of the instrument in FIG. 25;
FIG. 27 is a flowchart of an exemplary method;
FIG. 28 is a table of results of testing using an exemplary device;

DETAILED DESCRIPTION

Figure 1:
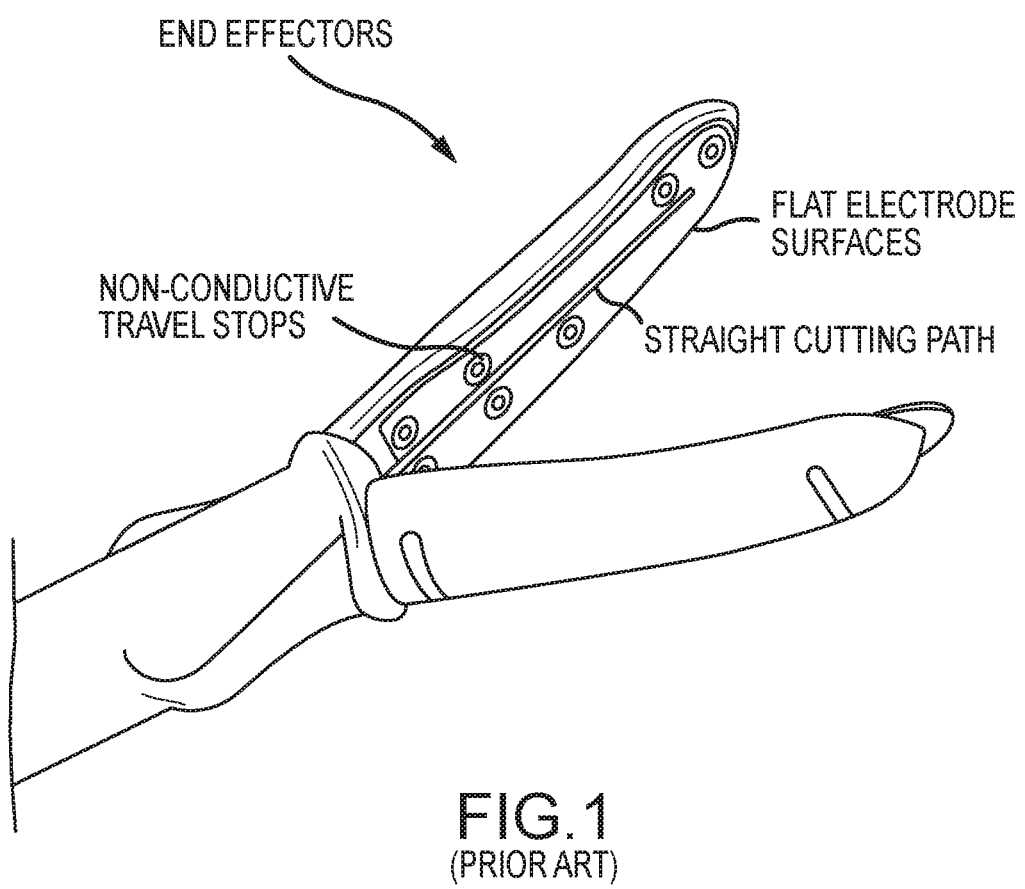

As previously alluded in the background of this document, and as illustrated in FIG. 1, the known prior art devices such as the LigaSure provide a high power tissue sealing and cutting device. These and similar high power devices, such as the device described in U.S. Pat. No. 6,033,399 to Gines, apply over 100 Watts of power to the tissue to seal. The LigaSure tool is known to apply over 180 Watts of tissue to the tissue to seal. Such high power applications result in a phenomenon known as lateral thermal spread, which is the spread of energy, heat, and charring to nearby and unintended tissue, meaning that the high power devices are not eligible for certain regulatory safety ratings.

To meet the need for a device that is eligible for these regulatory safety ratings, the Applicants generally determined that a low power device having certain parameters can be utilized to reliably and safely seal tissue. These teachings are published in co-owned U.S. Pat. No. 9,265,561 (the '561 patent), to Kennedy et al., and discloses a system and method for sealing tissue at low powers. The entire contents of the '561 patent are incorporated herein by reference in their entirety as if fully set forth herein.

In a related patent, co-owned U.S. Pat. No. 9,039,694 (the '694 patent), to Ross et al., discloses a system and method for providing power to an electrosurgical instrument. The entire contents of the '694 patent are incorporated herein by reference in their entirety as if fully set forth herein.

The teachings of the following U.S. Patents are incorporated by reference herein for all proper purposes: U.S. Pat. No. 5,876,401 to Schulze, U.S. Pat. No. 6,174,309 to Wrublewski, U.S. Pat. No. 6,458,128 to Schulze, U.S. Pat. No. 6,682,528 to Frazier, U.S. Pat. No. 7,083,618 to Couture, U.S. Pat. No. 7,101,373 to Dycus, U.S. Pat. No. 7,156,846 to Dycus, U.S. Pat. No. 7,101,371 to Dycus, U.S. Pat. No. 7,255,697 to Dycus, U.S. Pat. No. 7,722,607 to Dumbauld, U.S. Pat. No. 8,540,711 to Dycus, U.S. Pat. No. 7,131,971 to Dycus, U.S. Pat. No. 7,204,835 to Latterell, U.S. Pat. No. 7,211,080 to Treat, U.S. Pat. No. 7,473,253 to Dycus, U.S. Pat. No. 7,491,202 to Odom, U.S. Pat. No. 7,857,812 to Dycus, U.S. Pat. No. 8,241,284 to Dycus, U.S. Pat. No. 8,246,618 to Bucciaglia, U.S. Pat. No. 8,361,072 to Dumbauld, U.S. Pat. No. 8,469,956 to McKenna, U.S. Pat. No. 8,523,898 to Bucciaglia, U.S. Pat. No. 8,579,894 to Falkenstein, U.S. Pat. No. 8,968,311 to Allen, U.S. Pat. No. 9,011,437 to Woodruff, U.S. Pat. No. 9,028,495 to Mueller, U.S. Pat. No. 9,113,901 to Allen, U.S. Pat. No. 5,800,44 to Wales, U.S. Pat. No. 5,462,546 to Rydell, U.S. Pat. No. 5,445,638 to Rydell, U.S. Pat. No. 5,697,949 to Giurtino, U.S. Pat. No. 5,797,938 to Parashac, U.S. Pat. No. 6,334,860 to Dorn, U.S. Pat. No. 6,458,130 to Frazier, U.S. Pat. No. 6,113,598 to Baker, and U.S. Pat. No. 6,033,399 to Gines.

The teachings of the following U.S. Patent Publications are incorporated by reference herein for all proper purposes: US2014/0031819A1 to Dycus, US2015/0250531A1 to Dycus, US2015/0133930 to Allen, US2013/0131651 to Strobl, US2014/0257285 to Moua, US2007/0173813 to Odom, US2009/0076506 to Baker, US2005/0010212 to McClurken, US2007/0173804 to Wham, and US2007/0156140 to Baily.

The teaching of the following European publication is incorporated by reference herein for all proper purposes: EP0986990A1 to Eggers.

Applicants have developed a device that can safely seal and cut tissue, that not only functions reliably at low powers, but also result in a significantly smaller footprint of affected tissue. That is, Applicants' device is not prone to cause stray burns to tissue near a surgical site, thereby providing a tool that is eligible for certain regulatory safety ratings.

Turning now to FIG. 2, it illustrates a device 100 for a surgical instrument for cutting and sealing tissue. The device 100 may be referred to as an end effector, and has an upper jaw 102, a lower jaw 104, a cutting mechanism 106 (see FIG. 8), a linkage mechanism 108 for enabling manipulation of the jaws 102, 104, and an electrosurgical control mechanism 110. In some embodiments, the device 100 may be configured to apply bipolar power to tissue clamped between the jaws 102, 104, and may be referred to as a bipolar device 100. For ease of reference, it is noted that a proximal portion of the device 100 is illustrated to the left in FIG. 2 and a distal portion of the device 100 is illustrated to the right in FIG. 2.

The jaws 102, 104 may be curved to a right or a left of an X-Y plane defined by a longitudinal axis X and a vertical axis Y, in a manner that may be conducive to grasping, dissecting, manipulating and/or retracting tissue. That is, a longitudinal axis X may be defined by a straight line, while a sealing axis W may be curved two- or three-dimensionally. In the embodiment illustrated in FIG. 2, the sealing axis W is curved two-dimensionally. See also FIG. 6.

In some embodiments, the jaws 102, 104 are configured to selectively apply a surgical power for sealing tissue at power levels in a manner similar to that illustrated or described in the '561 patent). The jaws 102, 104 may also comprise material or other design selections as disclosed in the '561 patent and/or the '694 patent. In the embodiment illustrated, overmolding 160 is illustrated transparently, and those skilled in the art will understand that the overmolding 160 may be provided about a number of features, for aesthetic purposes and/or for electrical isolation.

Figure 8:
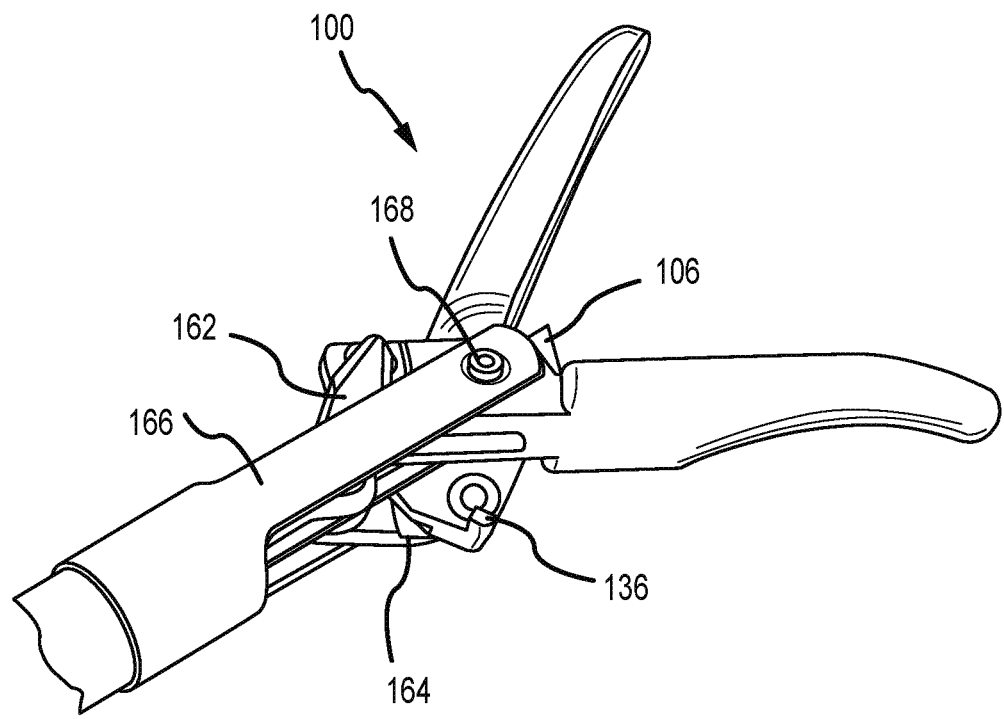
Figure 9:
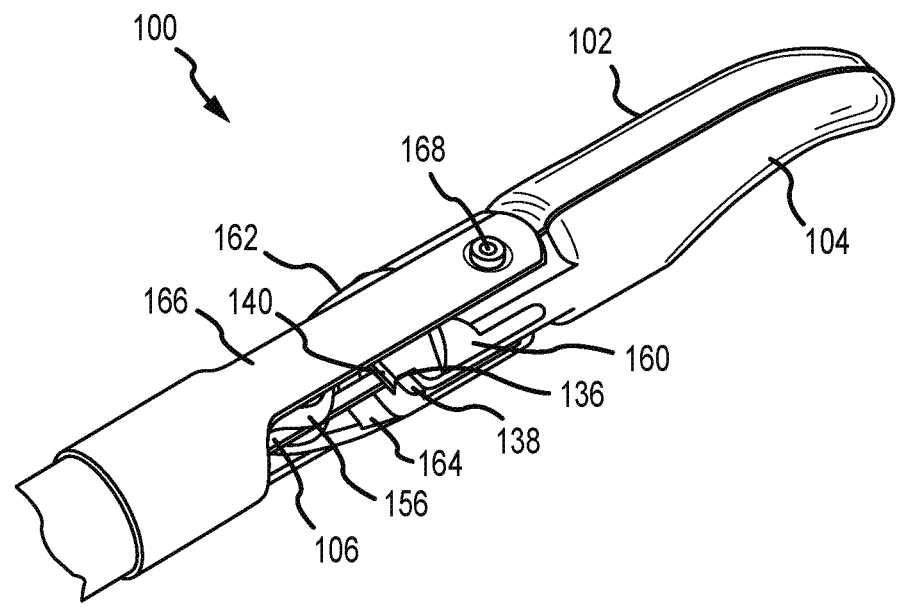
Figure 10:
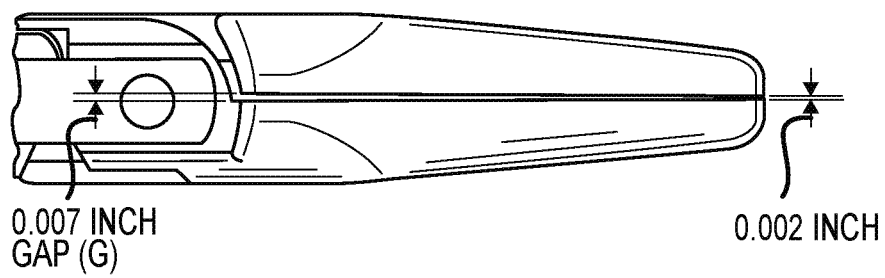

In some embodiments, and as illustrated in FIG. 9, one or both of the jaws 102, 104 may have a non-conductive travel stop 112 at or near a distal portion 126, 130 of the jaw(s) 102, 104, and a jaw interlock feature 136 at a proximal region, to prevent the jaws 102, 104 from over-rotation (see FIGS. 2, 8, 9). In some embodiments, the jaw interlock feature 136 may comprise a protrusion 138 on a first jaw 102 that is configured to abut a flange, ridge, or other surface 140 on a second jaw 104. The jaw interlock feature 136, in combination with the non-conductive protrusion(s) 112, may prevent the jaws 102, 104 from clamping too tightly about tissue therebetween. In some embodiments, and as most clearly illustrated in FIG. 10, the jaws 102, 104 may be configured to maintain a gap G of between about 0.007 inches (or about 0.178 millimeters) and about 0.002 inches (or about 0.051 millimeters) between the primary sealing surfaces 142, 143 of the jaws 102, 104 even in the closed position without tissue clamped therebetween. In some embodiments, the jaws 102, 104 have a tip bias; that is, a distal portion, such as the travel stop(s) 112, of the jaws 102, 104 may be configured to make contact or stop traveling towards closure while a proximal portion has a gap G of at least 0.005 inches (or about 0.127 millimeters), and/or the distal portion of the gap G is less than the proximal portion of the gap G. A portion of one or both of the jaws 102, 104 between the protrusion(s) 112 and the jaw interlock feature 136 may flex during clamping. Therefore, those skilled in the art will understand that the gap G is determined prior to application of a full clamping force on tissue; instead, the gap G is calculated or defined at initial contact. In some embodiments, another travel stop 112 may be provided at a different region to further ensure the jaws 102, 104 do not contact or short.

Figure 9A:
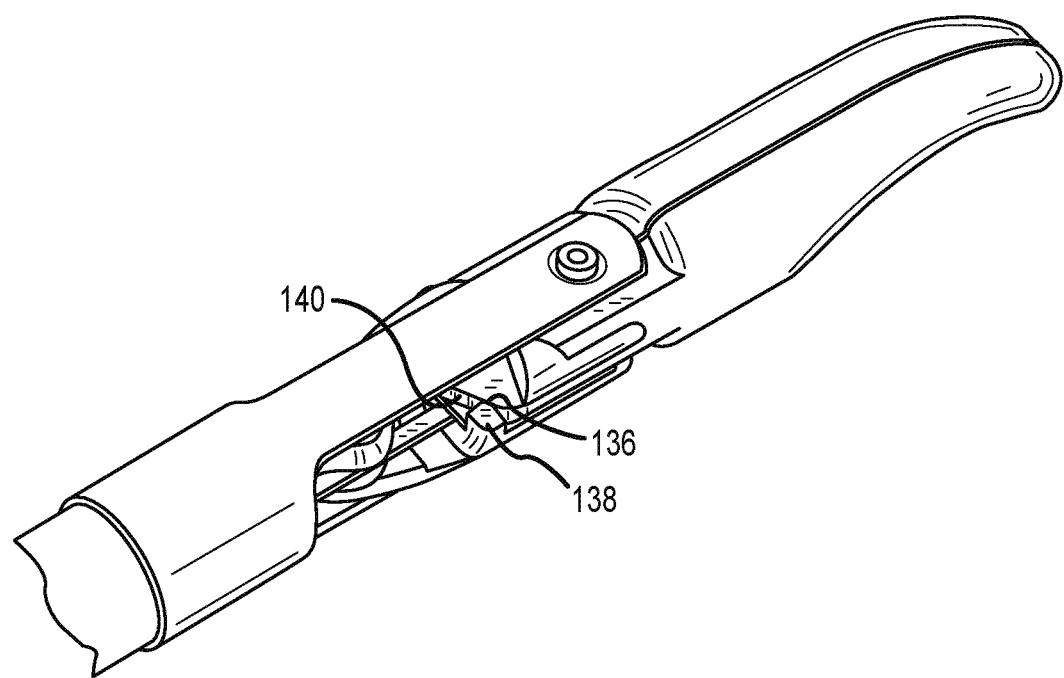

FIG. 9A illustrates the device of FIG. 9 with a variant of the jaw interlock feature 136, protrusion 138, and flange, ridge, or other surface 140. Those skilled in the art will recognize that these features functions substantially as those illustrated in FIG. 9.

In some embodiments, the device is configured to maintain a gap G between the primary sealing surfaces 142, 143 of between about 0.2 millimeters and about 0.05 millimeters. In some embodiments, the gap G is between about 0.16 and about 0.20 millimeters at the proximal portion. In some embodiments, the gap G is between about 0.05 millimeters and about 0.07 millimeters at the distal portion. In some embodiments, the gap G is at least 0.07 millimeters. In some embodiments, the gap G continuously decreases from the proximal portion to the distal portion.

In some embodiments, the device is configured to maintain a gap G between the primary sealing surfaces 142, 143 of between about 0.25 millimeters and about 0.03 millimeters. In some embodiments, the gap G is between about 0.16 and about 0.25 millimeters at the proximal portion. In some embodiments, the gap G is between about 0.03 millimeters and about 0.07 millimeters at the distal portion.

Turning now to FIGS. 3-4, in some embodiments, one or both of the jaws 102, 104 may include a channel 114, 116 shaped and positioned such that, when the jaws 102, 104 are in a closed position as illustrated in FIGS. 3-4, the channel(s) 114, 116 and jaws 102, 104 define a travel path 118 through which the tissue cutting mechanism 106 or knife may travel to cut tissue after it has been sealed. The channel(s) 114, 116 or elongated slot(s) may be non-linear, such that the knife or cutting mechanism travels a non-linear path to sever tissue.

Figure 6:
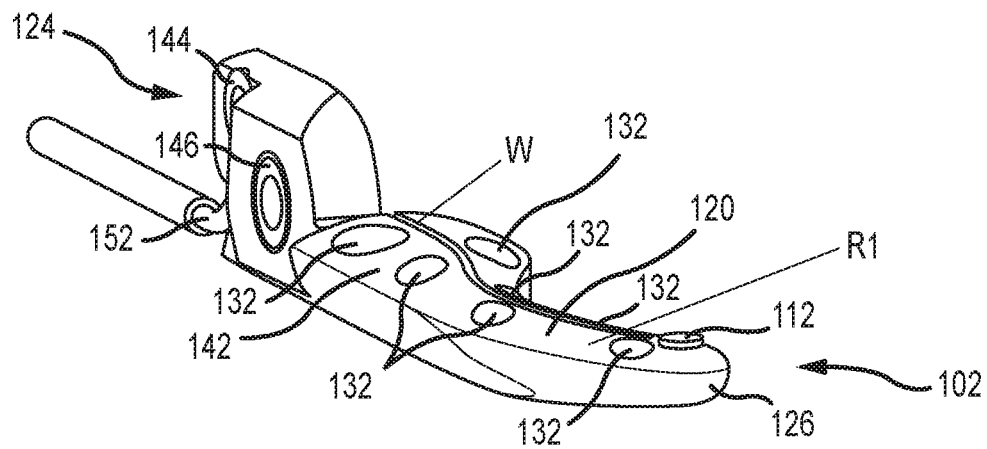

As illustrated in FIG. 6, in some embodiments, a first jaw 102 may have a first sealing surface 120, a primary sealing surface 142 of which has a generally convex shape. In some embodiments, a portion of the first jaw 102 may have a first sealing surface 120 with a first curvature R1 about a sealing axis W. In some embodiments, the sealing axis W is defined by the travel path 118 of the cutting mechanism 106. That is, the first curvature R1 may be relative to the travel path 118. In some embodiments, the first curvature R1 is constant from a proximal portion 124 of the first jaw 102 to a distal portion 126 of the first jaw 102. In some embodiments, the first curvature R1 is greater at a proximal portion 124 of the first jaw 102 than at a distal portion 126 of the first jaw 102. In some embodiments, the first curvature R1 is defined by a circle of radius R1. In some embodiments, the first curvature R1 is defined by an elliptical function.

Figure 7:
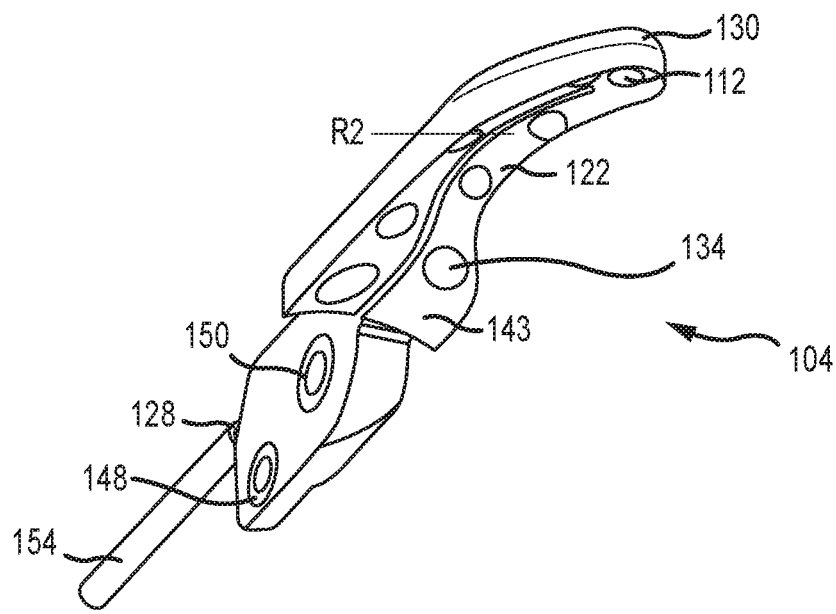

As illustrated in FIG. 7, relatedly, a second jaw 104 may have a second sealing surface 122, a primary sealing surface 143 of which has a generally concave shape, or otherwise shaped and configured to receive the first jaw 102. In some embodiments, a portion of the second jaw 104 may have a second sealing surface 122 with a second curvature R2 about the sealing axis W and/or travel path 118 of the cutting mechanism, the second curvature R2 greater than the first curvature R1. In some embodiments, the second curvature R2 is constant from a proximal portion 128 of the second jaw 104 to a distal portion 130 of the second jaw 104. In some embodiments, the second curvature R2 is greater at a proximal portion 128 of the second jaw 104 than at a distal portion 130 of the second jaw 104. In some embodiments, the second curvature R2 is defined by a circle of radius R2. In some embodiments, the second curvature R2 is defined by an elliptical function.

Returning to FIG. 6, either of the first jaw 102 and/or the second jaw 104 may have a current concentrator surface 132, 134, which may be one or more conductive protrusions 132 and or recesses 134 shaped and configured to direct electrosurgical energy towards particular areas of the sealing surfaces 122, 124. In some embodiments, the total power applied to the jaws 102, 104 may be substantially as described in the '561 and/or the '694 patents. The conductive protrusions 132 may be in a variety of shapes and sizes as illustrated, and may have one or more curved surfaces thereon, with one or more radii of curvature, elliptical functions, or other nonlinear functions.

Figure 11:
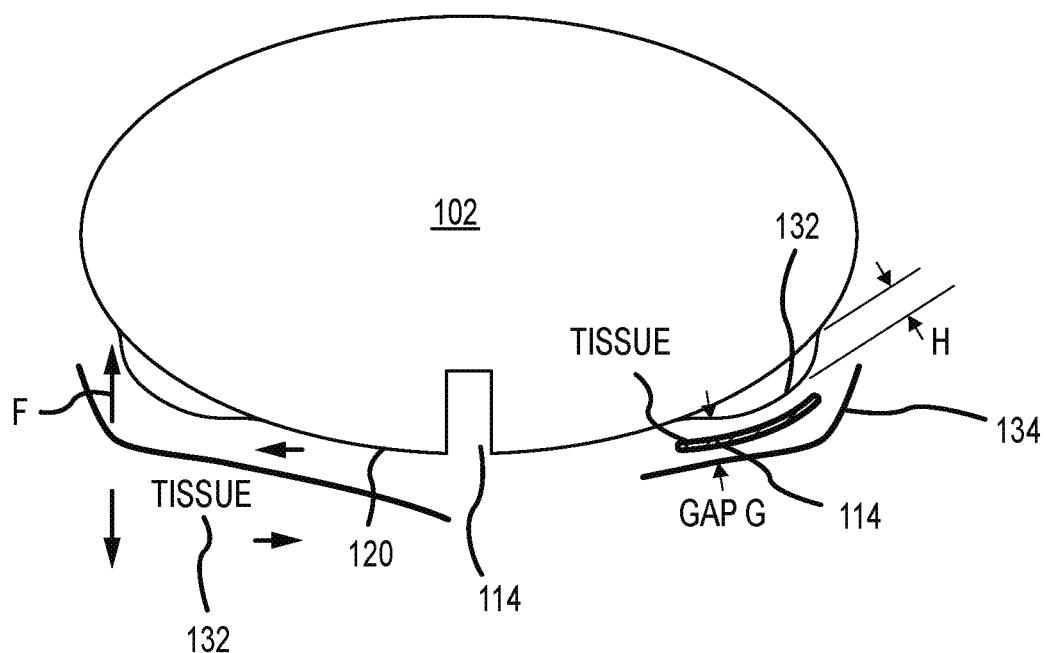

As illustrated in FIG. 11, in some embodiments, a height H of the protrusion(s) 132 from the primary seal surface 120 is between about 0.001 inches and about 0.0025 inches (or between about 0.0254 millimeters and about 0.0635 millimeters). The height H is selected to be sufficient to induce an energy concentration without introducing potential weakened or thinned spots in tissue that is sealed using the device 100. In some embodiments, the height H is between about 0.015 millimeters and about 0.080 millimeters. In some embodiments, the height H is between about 0.03 millimeters and about 0.06 millimeters. Those skilled in the art will understand that the height H and or depth D should be configured so as to not allow the jaws 102, 104 to contact each other and/or to induce sparking between the jaws. In some embodiments, a gap G of at least about 0.002 inches, or at least about 0.051 millimeters, is maintained between the jaws 102, 104.

In some embodiments, a height H of a first protrusion is greater than a height H of a second protrusion. In some embodiments, a height H of a protrusion at a proximal region of the jaw 102, 104 is greater than a height H of a protrusion closer to the distal region of the jaw 102, 104. In some embodiments, a protrusion 132 closer to the proximal region of the jaw 102, 104 may have a circular portion with a radius of curvature that is less than a circular portion of a protrusion 132 closer to the distal region of the jaw 102, 104. In some embodiments, a protrusion 132 closer to the proximal region may be configured to induce a sharper current concentration than does a protrusion 132 closer to the distal region.

As further illustrated in FIG. 11, a gap G between the protrusion(s) 132 and the second jaw or recess 134 may be held consistent. That is, in some embodiments, a protrusion 132 on a first jaw 102, 104 corresponds to a recess 134 on a second jaw 102, 104, to maintain a gap G. In some embodiments, the gap G is about 0.002 inches between the primary sealing surfaces 142, 143 and the current concentrators (protrusion/recess 132, 134). In some embodiments, a relief between a protrusion 132 or recess 134 and a primary sealing surface 142, 143 is provided, so as to not induce sparking at sharp corners.

In some embodiments, a single protrusion 132 is provided on one of the jaws 102, 104. In some embodiments, two protrusions 132 are provided on the jaws 102, 104.

Returning again to FIG. 7, either or both of the first jaw 102 or the second jaw 104 may have more conductive recesses 134 shaped and configured to direct electrosurgical energy towards particular areas of the sealing surfaces 122, 124. The conductive recesses 134 may be in a variety of shapes and sizes as illustrated, and may have one or more curved surfaces thereon, with one or more radii of curvature. The conductive recesses 134 may corresponding to opposing ones of the conductive protrusions 132, and some or all of the conductive protrusions 132 may nestle in the conductive recesses 134. In some embodiments, all of the conductive protrusions 132 are on the first or second jaw 102, 104, and all of the conductive recesses 134 are on the other one of the first or second jaw 102, 104. In some embodiments, some of the conductive protrusions 132 are on one of the jaws 102, 104, and some of the conductive protrusions 132 are on the other of the jaws 102, 104. Respective conductive recesses 134 may be similarly distributed and placed. The conductive recesses 134 may be in a variety of shapes and sizes as illustrated, and may have one or more curved surfaces thereon, with one or more radii of curvature, elliptical functions, or other nonlinear functions.

The conductive recesses 134 may have a depth corresponding to the height H of the protrusion(s) 132, again to ensure that an energy concentration is induced without introducing potential weakened or thinned spots in tissue that is sealed using the device 100.

In some embodiments, the depth is between about 0.015 millimeters and about 0.080 millimeters. In some embodiments, the depth is between about 0.03 millimeters and about 0.06 millimeters. In some embodiments, a depth of a first recess 134 is greater than a depth of a second recess 134. In some embodiments, a depth of a recess at a proximal region of the jaw 102, 104 is greater than a depth of a recess closer to the distal region of the jaw 102, 104. In some embodiments, a recess 134 closer to the proximal region of the jaw 102, 104 may have a circular portion with a radius of curvature that is less than a circular portion of a recess 134 closer to the distal region of the jaw 102, 104. In some embodiments, a recess 134 closer to the proximal region may be configured to induce a sharper current concentration than does a recess 134 closer to the distal region.

One or more conductive protrusions 132, and, optionally, conductive recesses 134 may be provided so as to induce an energy concentration at the protrusion 132 and recess 134, and may be referred to as energy or current concentrators. That is, the conductive protrusions 132 do not necessarily have corresponding recesses 134. By inducing this energy concentration, Applicants have provided an improved method of sealing tissue—specifically, the current concentration at each protrusion/recess 132, 134 interface is configured to induce an initial flow of energy between the jaws 102, 104 before allowing the energy to flow across the entire respective surfaces 120, 122. In turn, the overall power requirements for the system 100 are lowered, yet still provides the ability to seal relatively large tissue sections at a low power, such as at 40 Watts or less, or at other power levels and current concentrations as described in the '561 patent. In some embodiments, the device 100 is configured to deliver a power of 50 Watts or less. In some embodiments, the device 100 is configured to deliver a power of 40 Watts or less. In some embodiments, the device 100 is configured to deliver a power of 35 Watts or less. In some embodiments, the device 100 is configured to deliver a power of 20 Watts or less. In some embodiments, the device 100 is configured to deliver a current of 3 Amperes or less. In some embodiments, the device 100 is configured to deliver a current of 2.5 Amperes or less. The current or energy concentrators may be shaped so as to concentrate current without inducing sparking.

In some embodiments, the instrument 100 is shaped to pass through a cannula having an inner diameter of 6 millimeters or less.

Moreover, the protrusions/recesses 132, 134 and/or the curved sealing surfaces 120, 122 reduce or eliminate the chances of tissue sticking to the jaws 102, 104 after a seal is complete, without the use of exotic materials in the jaws 102, 104. That is, the jaws 102, 104 including the protrusions 132 and recesses 134 may be made of a surgical stainless steel without any non-stick coating applied thereto. For example, the protrusions 132 and/or the recesses 134 may be shaped and/or positioned so as to initiate a concentrated pulling-away effect on relatively targeted regions of tissue as the jaws 102, 104 are opened, thereby improving separation. In some cases, the protrusions 132 and/or the recesses 134 may be shaped and/or positioned so as to apply a separating force on targeted regions of tissue that is greater than a separating force on non-targeted regions of tissue (e.g. tissue that is further from the protrusions 132 and/or the recesses 134, such as tissue between the primary sealing surfaces 142, 143). In some embodiments, a gap between one or more of the conductive protrusions 132 and one or more recesses 134 is less than the gap G between the primary sealing surfaces 142, 143 of the jaws 102, 104.

In some embodiments, the jaw(s) 102, 104 may have a sealing surface 120, 122 with a sealing surface area of 24 square millimeters or less. In some embodiments, the jaw(s) 102, 104 may have a sealing surface 120, 122 with a sealing surface area of 10 square millimeters or less.

Continuing with FIGS. 6-7, the device 100 may provide a curved travel path 118 through which the cutting mechanism may pass, such as after effectuating a seal on tissue clamped between the jaws 102, 104. Those skilled in the art will understand that, in some embodiments, to travel down the travel path 118, the cutting mechanism 106 may be flexible (e.g. a knife that bends), and/or the width of the channels 114, 116 may be suitably wide enough to allow the cutting mechanism 106 to pass therethrough without bending. The channels 114, 116 may be curved in some embodiments, and as illustrated. In some embodiments, the channels 114, 116 and cutting path 118 may be substantially linear. In some embodiments, the cutting mechanism 106 is flexible. In some embodiments, the cutting mechanism 106 is relatively rigid.

Figure 14:
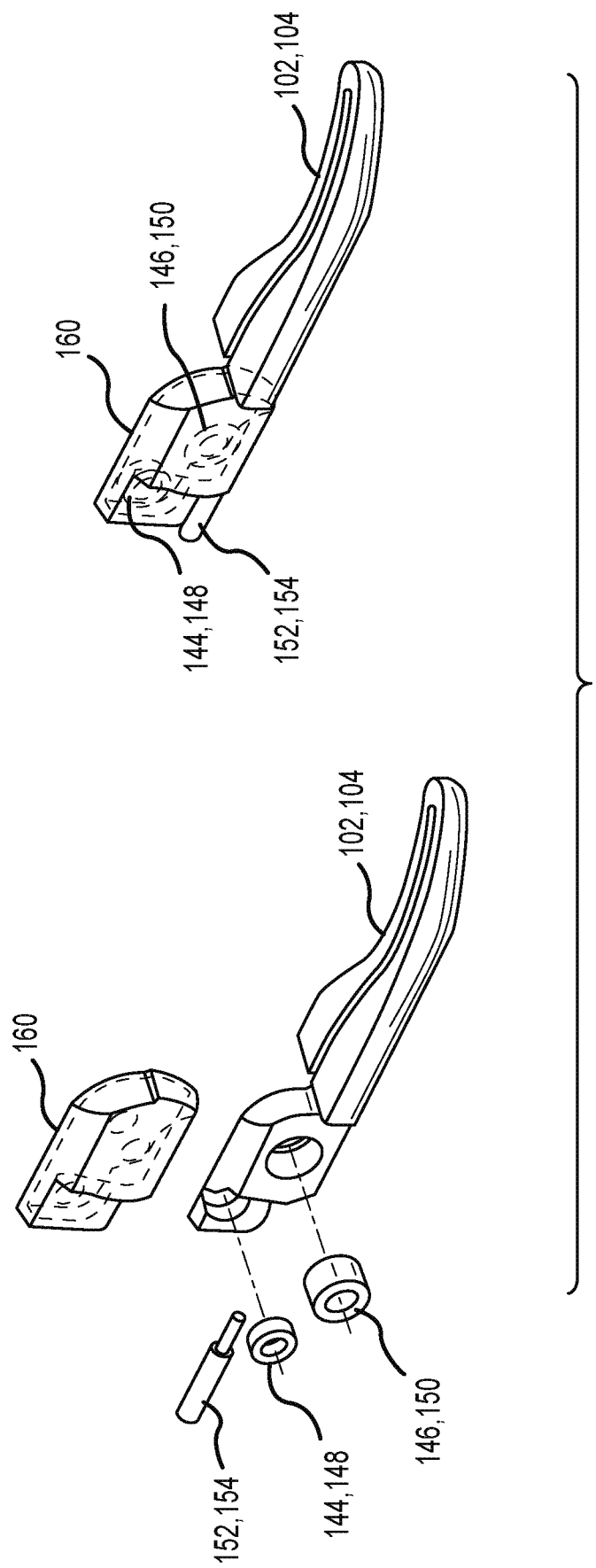

In some embodiments, the cutting path 118 defines a length of stroke S (of the cutting mechanism 106), as illustrated in, for example, FIG. 14. The length of stroke S may extend all the way through the sealing portions of the jaws 102, 104. That is, the cutting path 118 may be shaped and positioned so as to allow a single stroke of the cutting mechanism 106 to cut all the way through tissue held between the jaws 102, 104. In some embodiments, the length of stroke S may only extend partially through the sealing portions of the jaws 102, 104.

In some embodiments, the channels 114, 116 and/or cutting path 118 generally may include one or more stop features (not illustrated), so as to allow a user to adjust the length of stroke S relative to the jaws 102, 104. In some embodiments, the channels 114, 116 and/or cutting path 118 generally may include one or more tactile feedback features (not illustrated) that provide tactile feedback to the user. The tactile feedback features may provide the user with the ability to stroke the cutting mechanism 106 less than the entire length of stroke S or less than the entire length of sealed tissue in a first stroke, optionally open the jaws 102, 104 to optionally confirm that the tissue has been properly sealed, and then, optionally after re-closing the jaws 102, 104 to stroke the cutting mechanism 106 in a second stroke a distance that is greater than the first stroke. In some embodiments, the tactile feedback mechanism provides the user the apply sense or feel the length of stroke of more than two strokes having more than two lengths. The tactile feedback mechanism may include one or more ridges, dimples, detents, and/or any other tactile feedback means now known or as-yet to be developed, and suitable for indicating a general position of the cutting mechanism 106 relative to the jaws 102, 104.

Continuing with FIGS. 6-7, a coated conductive medium, which may be a wire 152, terminating at the first jaw 102, and a coated conductive medium, which may be a wire 154, terminating at the second jaw 104 provide an energy path through the jaws 102, 104. The wires 152, 154 may be soldered or welded to the jaws 102, 104. In some embodiments, the wires 152, 154 may be coupled to the jaws 102, 104 by way of an insulation-displacement contact or insulation piercing contact in a manner known to those skilled in the art. In some embodiments, an overmold 160 may be provided about the wires 152, 154 and other features of the device 100.

As most clearly illustrated in FIGS. 8-9, a cutting mechanism 106 having a distal knife portion and a proximal rod portion may be configured to travel within a split rod 156. While the cutting mechanism 106 itself may function substantially as is known in the industry, those skilled in the art will recognize that having the cutting mechanism 106 positioned interior of the split rod 156 may allow for a smaller footprint device 100.

As previously alluded in this document, in some embodiments, a relatively small sealing/cutting device 100 may be provided. For example, in some embodiments, the device 100 may have an overall envelope of less than 3.0 millimeters and/or be configured to fit within a cannula of 3.5 millimeters. In some embodiments, the device 100 may have an envelope of less than 5.0 millimeters and/or may be configured to fit within a cannula of 5.5 millimeters. In some embodiments, the device 100 may be configured to fit within a cannula of 7.5 millimeters. In some embodiments, the device 100 may be configured to fit within a cannula of 10.5 millimeters.

Those skilled in the art will recognize that a smaller device 100 such as that described herein must still provide the same clamping force on tissue as a larger device does, resulting in significant force concentrations at, for example, the interface between the jaws 102, 104 and the links 162, 164 controlling the jaws 102, 104. Therefore, in some embodiments, the jaws 102, 104 include a plurality of bushings 144, 146, 148, 150 (see FIGS. 6-7) made of a non-conductive non-compressible or low compression material. In some embodiments, the jaws 102, 104 comprise non-conductive or bushings 144, 146, 148, 150 to interface with the linkage mechanism 108 including links 162, 164 and a split rod 156. In some embodiments, the bushings 144, 146, 148, 150 isolate actuators such as the links 162, 164 from the conductive jaws 102, 104. In some embodiments, the bushings 144, 146, 148, 150 are ceramic. In some embodiments, one or more of the bushings 144, 146, 148, 150 comprise a thermoplastic polymer. In some embodiments, the thermoplastic polymer is injection molded. In some embodiments, one or more of the bushings 144, 146, 148, 150 comprise a thermoset polymer. In some embodiments, one or more of the bushings 144, 146, 148, 150 comprise a metal with an isolating surface treatment.

Those skilled in the art will recognize that the Applicants, in providing a small device that also meets FDA safety requirements, overcome significant industry challenges. Specifically, the question of how to provide a tissue sealing and dissection device while preventing burns to other tissue has been a challenge for some time, with numerous solutions attempted, including devices that cycle energy on and off, or devices that provide various forms of heat sinks or cooling materials. None of these devices, however, are suitable to a very small device (e.g. fitting a nominal 5 millimeter or a 6 millimeter canula). The Applicants provide a device with a bilateral jaw closure and potential heat sink capability with electrical isolation (such as, for example, by the use of anodized aluminum). In some embodiments, each bushing 144, 146, 148, 150 is configured to act as a heat sink and provide electrical isolation. This functionality may enable the provision of a device that can pass through a canula having a diameter of 6 millimeters or less, or, in some embodiments, a canula having a nominal diameter of 5 millimeters or less.

In some embodiments, a pin 168 passes through a pair of distal bushings 146, 150 in the jaws 102, 104, an elongated slot in the cutting mechanism 106, and the split shaft 166 to rotatably mount the jaws 102, 104 to the shaft 166. In some embodiments, protrusions in a pair of links 162, 164 engage a pair of proximal bushings 144, 148 in the jaws 102, 104 serve to translate opening/closing actions by a split rod 156 into rotating actions of the jaws 102, 104.

Turning now to FIG. 11, which illustrates a rough schematic of a cross-section of the first jaw 102, in some embodiments, the device 100 may be configured to apply a shear force F onto tissue as the jaws 102, 104 move away from each other after sealing tissue therebetween. In some embodiments, the conductive protrusions 132 and/or the conductive recesses 134 in the surfaces 120, 122 may be positioned such that the protrusions 132 and/or recesses 134 apply a shearing force F onto the tissue as the jaws 102, 104 are moved from a clamped or closed position towards an unclamped or open position. Those skilled in the art will understand that, where the protrusions 132 and/or recesses 134 are substantially circular or elliptical in nature, the shearing force F may be transverse, longitudinal and/or vertical relative to the travel path 118, thereby resulting in a concentrated shearing force F that initiates a separating of tissue from the jaws 102, 104. Once the separating is initiated, those skilled in the art will understand that separating of other portions of the tissue is made easier. Providing relatively smooth transitions between the protrusions 132 or recesses 134 and the primary sealing surfaces 142, 143 may avoid introducing an undesirable shift in the energy concentration.

Figure 12:
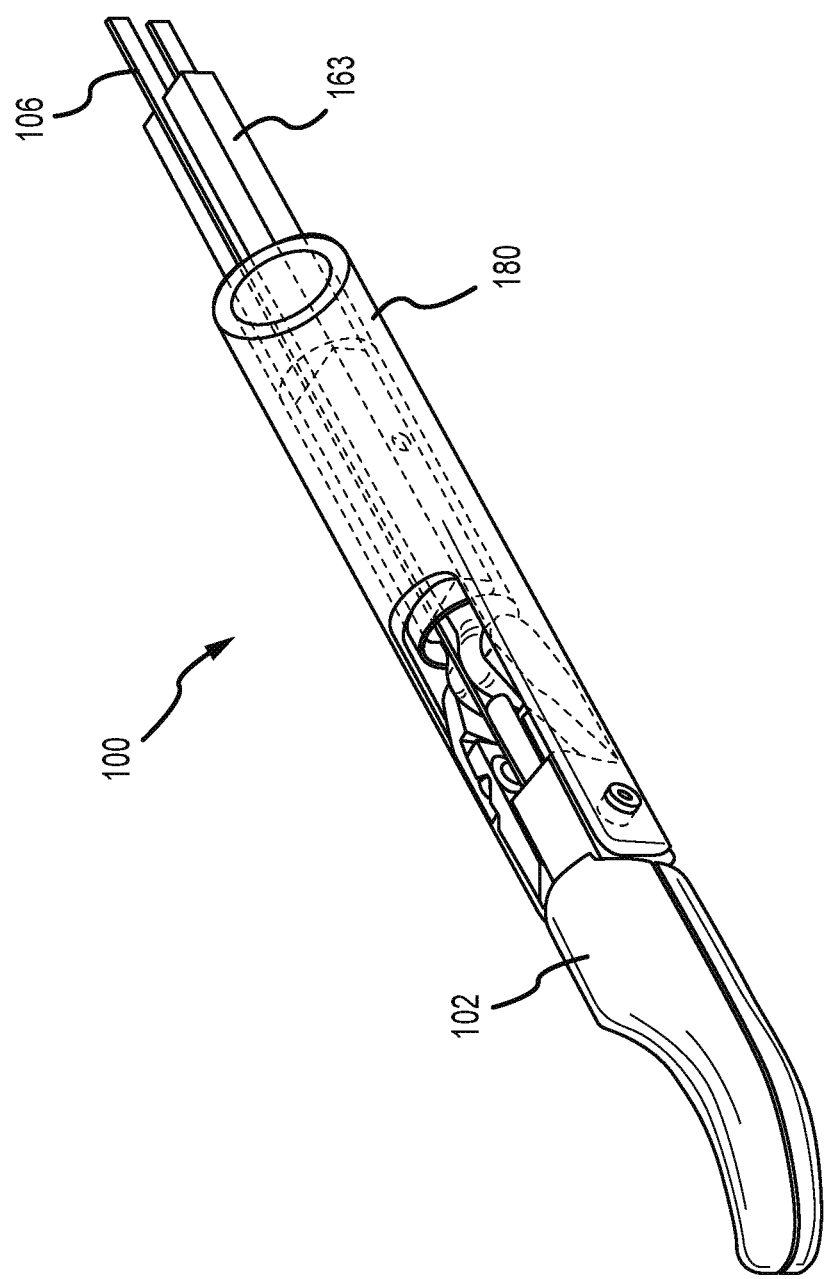

FIGS. 12, 13A, and 13B illustrate various views of an exemplary instrument 100, and, more specifically, how the jaws 102, 104 and cutting mechanism 106 or knife/knife pull rod might be operated, along with a pull rod 163 for the jaws and an outer housing or tube 180.

FIG. 14 illustrates one embodiment of how a coated wire 152, 154 might be affixed to a jaw 102, 104, such as, for example, by providing an overmold 160 that encloses a distal or exposed conductive portion of the wire 152, 154 and a proximal portion of the jaw 102, 104.

Figure 15:
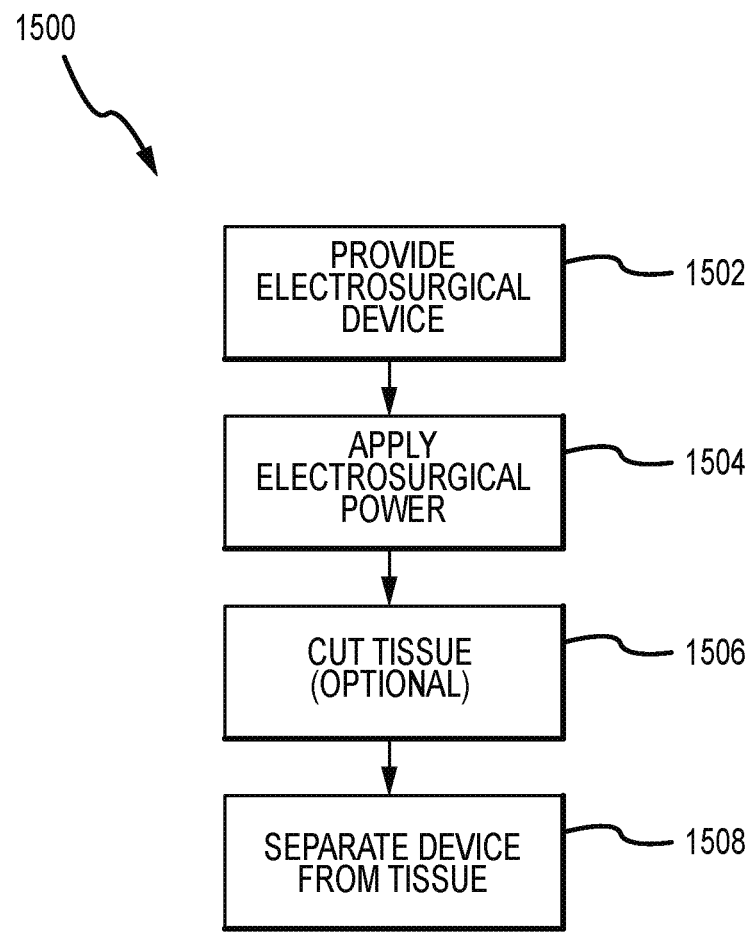

Turning now to FIG. 15, a method 1500 of sealing and cutting tissue is now disclosed in further detail. The method 1500 includes providing 1502 an electrosurgical cutter/sealer having a sealing surface with at least one feature configured to induce an energy concentration on the sealing surface. The method 1500 also includes applying 1504 electrosurgical power to tissue to be sealed, wherein applying 1504 electrosurgical power comprises distributing power unevenly across tissue clamped between a pair of jaws and/or clamping tissue between jaws in a manner that is tip-biased. The method 1500 may include cutting 1506 tissue clamped between the jaws; wherein cutting 1506 may include causing a cutting mechanism to travel a nonlinear path through the tissue. The method 1500 also includes separating 1508 the electrosurgical device from tissue clamped therebetween, wherein separating 1508 includes pulling the pair of jaws away from each other in a manner that causes a vertical and/or transverse shearing force to be applied to tissue clamped between the jaws.

The method 1500 may be achieved using a device as previously described with reference to FIGS. 2-11.

With reference now to FIGS. 16-19, the energy concentrators and/or the travel stops need not be present. That is, in some embodiments, a portion or substantially all of the curved sealing surfaces 120, 122 may be suitably curved so as to reduce or eliminate the chances of tissue sticking to the jaws 102, 104 after a seal is complete, without the use of exotic materials in the jaws 102, 104, and without energy concentrators. Other features of the exemplary device illustrated in FIGS. 16-19 may be substantially as otherwise described herein with reference to the device.

Figure 20:
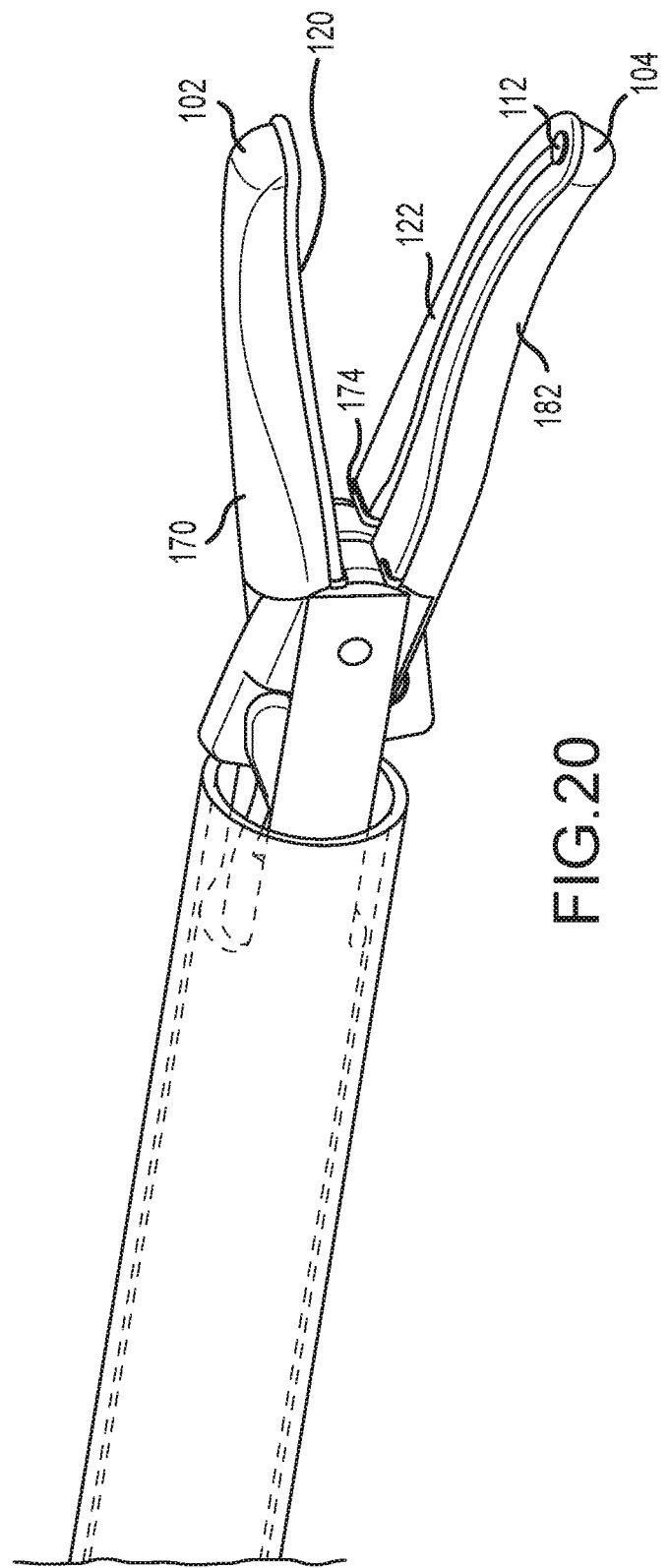

With reference now to FIG. 20, in some embodiments, all or a portion or a majority of the first and second sealing surfaces 120, 122 may be flat. In some embodiments, a substantial portion of one or both jaws 102, 104 may have a coating; for example, a substantial portion of the one or both jaws 102, 104 may be overmolded with a coating 170, 182. The coating may be made of a substantially nonconductive material. The coating 170, 182 may be applied by overmolding, plasma spraying, detonation spraying, wire arc spraying, thermal spraying, flame spraying, high velocity oxy-fuel spraying, high velocity air fuel spraying, warm spraying, or cold spraying.

In some embodiments, a travel stop 174 may be provided at or near a proximal region of one or both jaws 102, 104, so as to limit over-compression in a manner similar to that of the travel stop 112 previously described herein. In some embodiments, a travel stop 174 at the proximal region of a jaw may be formed from the coating 182. The travel stop 174 may be a flange in a proximal region of a jaw 102, 104. Those skilled in the art will recognize that, although FIG. 20 illustrates the stops 112, 174 positioned on the second jaw 104, either or both of the travel stops 112, 174 may be positioned on the first jaw 102. Those skilled in the art will recognize that either one or both travel stops 112, 174 may provide the necessary protection from over-compression.

Figure 21:
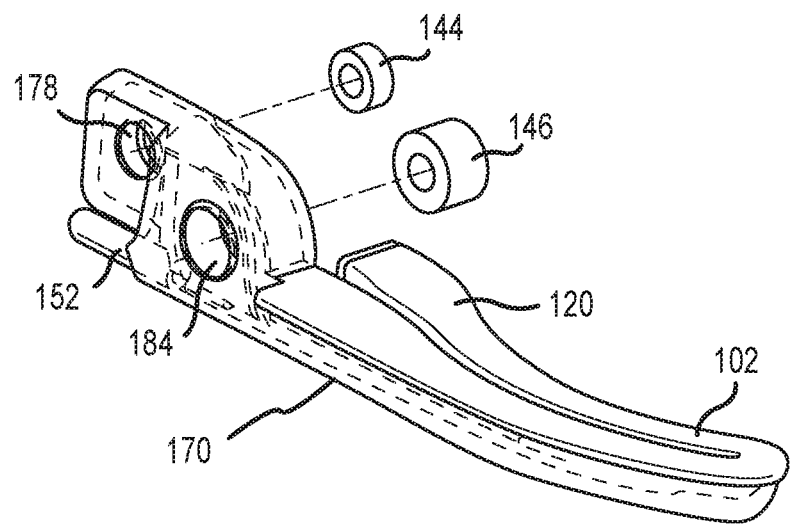
Figure 22:
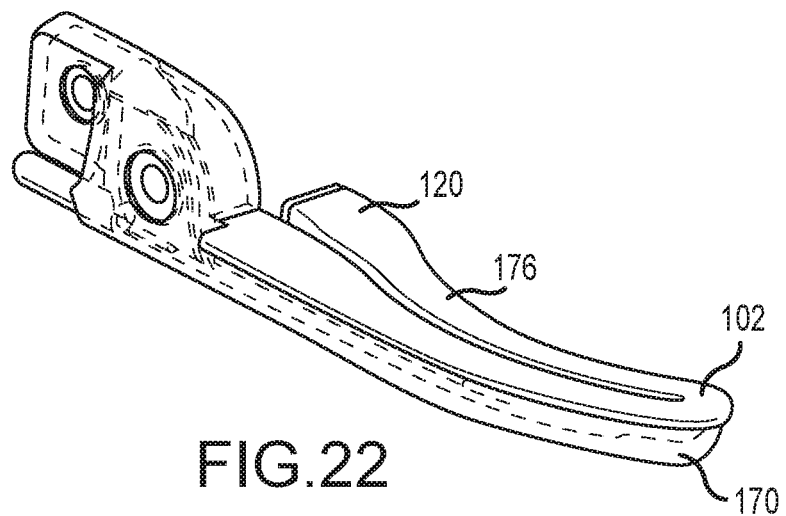

FIGS. 21-22 illustrate, respectively, disassembled and assembled views of an exemplary first jaw 102 suitable for use in the device 100. The jaw 102 may have a conductive core member 176 that is partially covered by a non-conductive coating 170. The core member 176 may have a sealing surface 120. In some embodiments, the sealing surface 120 may be flat as illustrated in FIGS. 21-22, or the sealing surface 120 may be curved and/or include conductive recesses and/or protrusions as previously described herein. The jaw 102 or core member 176 may include a plurality of recesses 178, 184 positioned in a proximal region of the core member 176. The recesses 178, 184 may be passages. The recesses 178, 184 may be shaped to receive bushings 144, 146, and may be positioned to enable control of a rotation of the jaw 102. As illustrated in FIGS. 21, 23 and FIGS. 6-7, both jaws 102, 104 may include a plurality of recesses 178, 184, 186, 188 shaped and positioned to enable rotation of both jaws 102, 104 relative to a control rod or cannula in a manner substantially as previously described herein. The coating 170 may position a conductive wire 152 to maintain contact with the core member 176 so as to conduct energy to the sealing surface 120. Although not illustrated in FIGS. 21-22, a proximal travel stop 174 may be provided as illustrated in FIG. 20.

Figure 23:
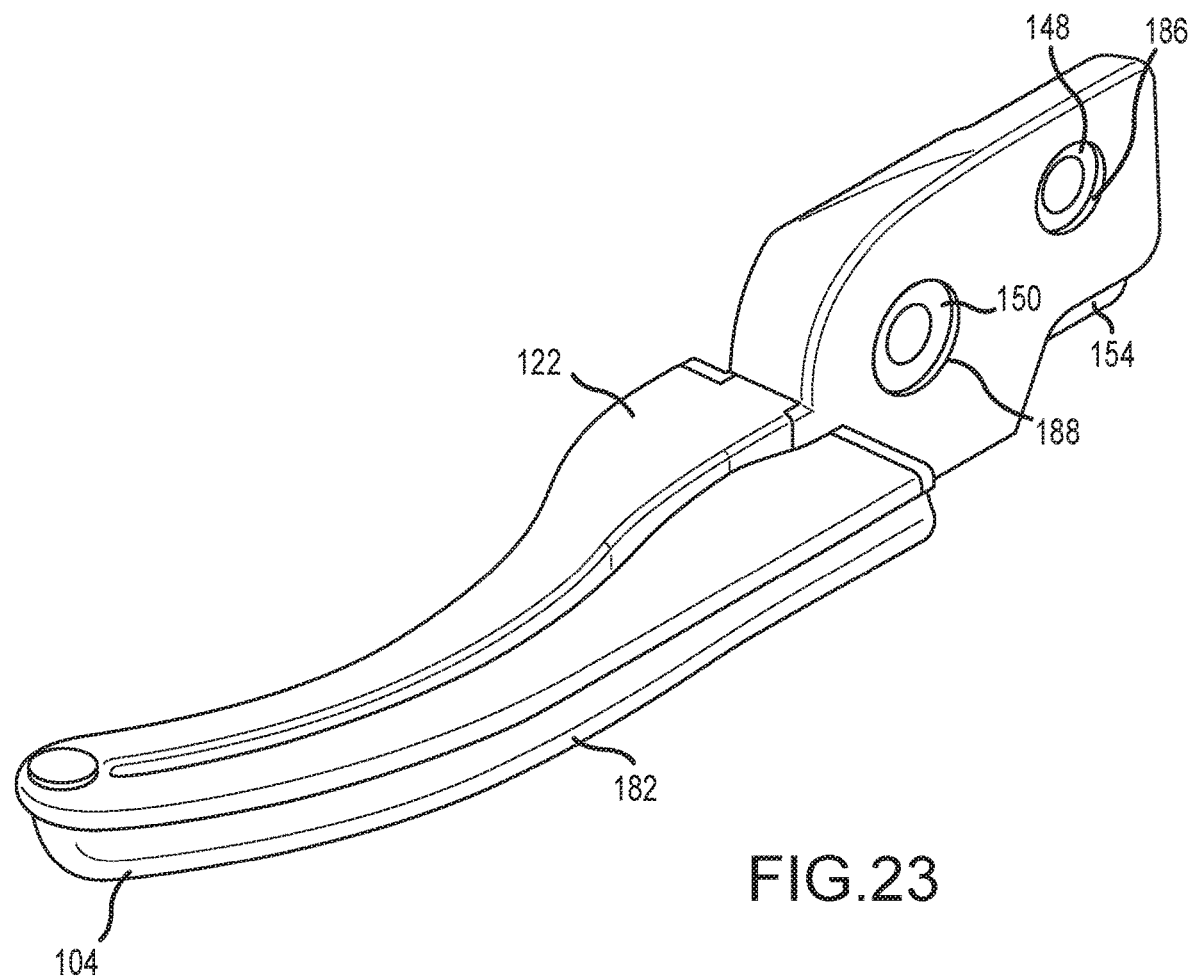
Figure 24:
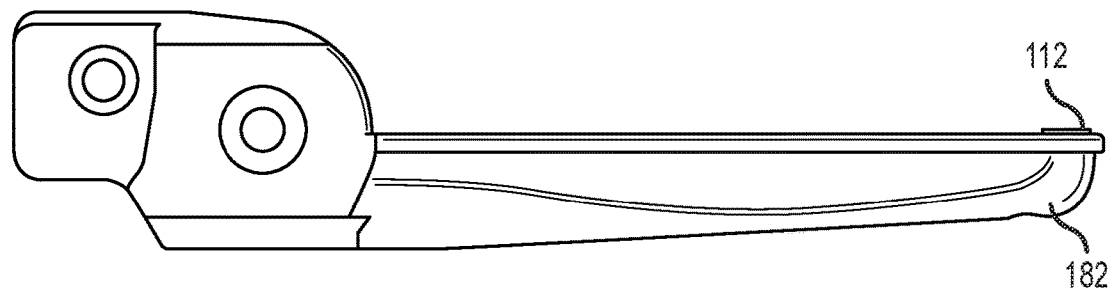

As illustrated in FIGS. 23-24, the second jaw 104 may be coated with a coating 182. The coating 182 may be applied and positioned in a manner substantially as previously described with reference to the first jaw 102. The second jaw 104 or the first jaw 102 may have a travel stop 112 at a distal region of the jaw 102, 104, and the travel stop 112 may have a height of up to about 0.003 inches, or up to about 0.08 millimeters. In some embodiments, a proximal portion of the jaw(s) 102, 104 may have a coating 170, 182 that is up to about 0.004 inches thick, or up to about 0.1 millimeters thick in a region near the recess(es) 178, 184, 186, 188. The recesses themselves may be free of the coating 170, 182. Although the second jaw 104 is illustrated with a distal travel stop 112 and not a proximal travel stop, those skilled in the art will recognize that a proximal travel 174 stop may be provided such as that illustrated in FIG. 20.

As described in reference to the previous figures, the device illustrated in FIGS. 20-24 may be configured to maintain a gap between the primary sealing surfaces 120, 122

Figure 25:
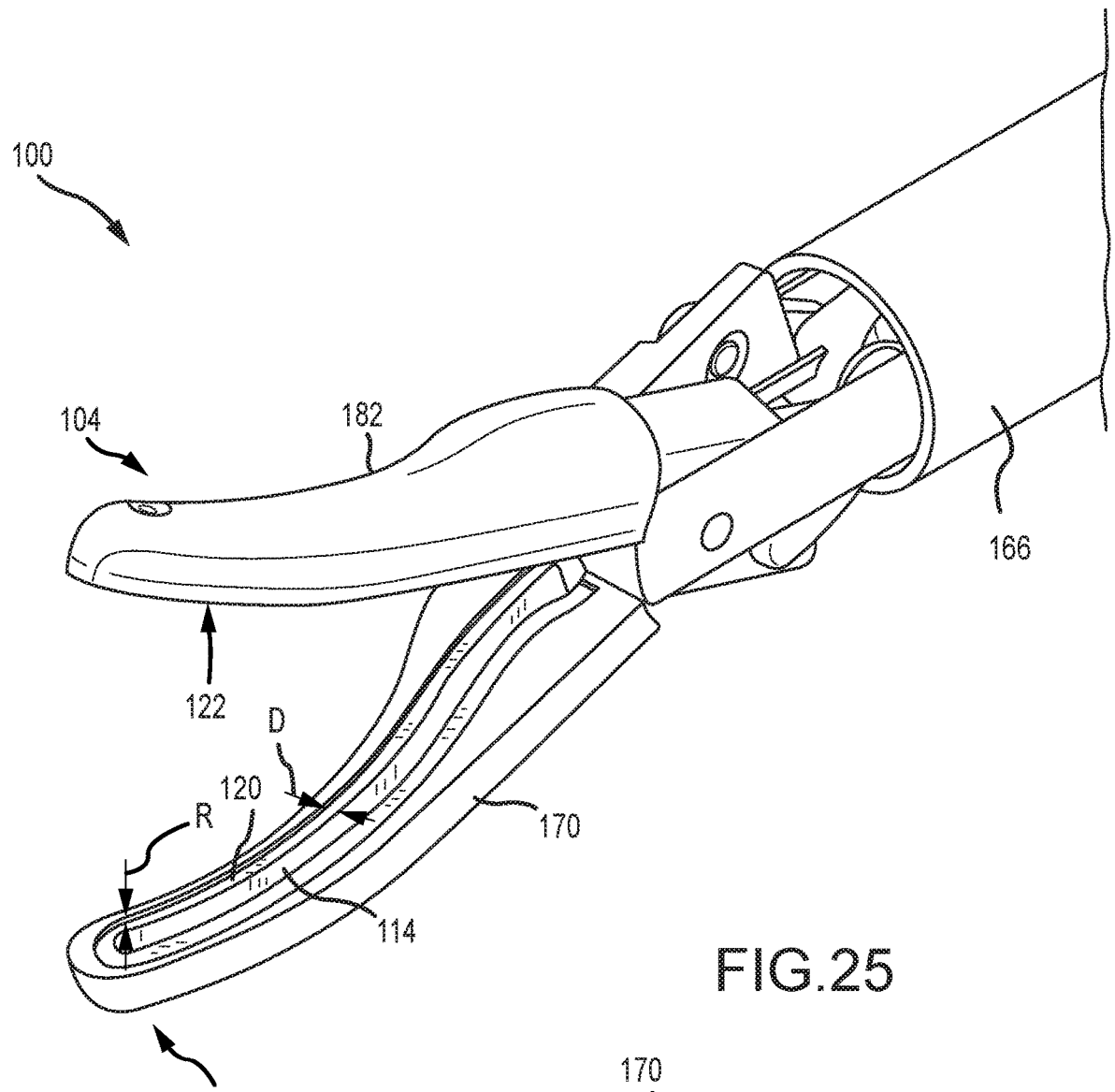
Figure 25A:
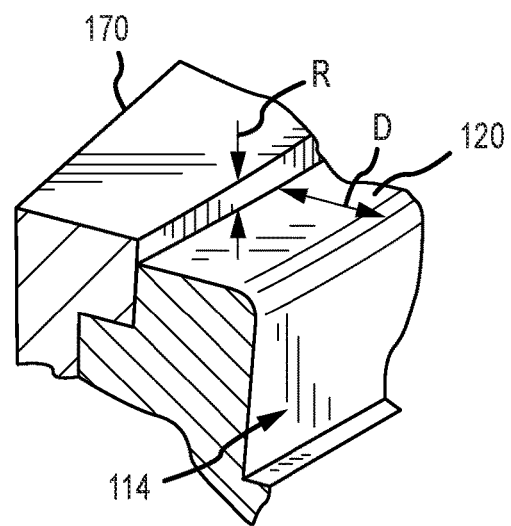
Figure 26:
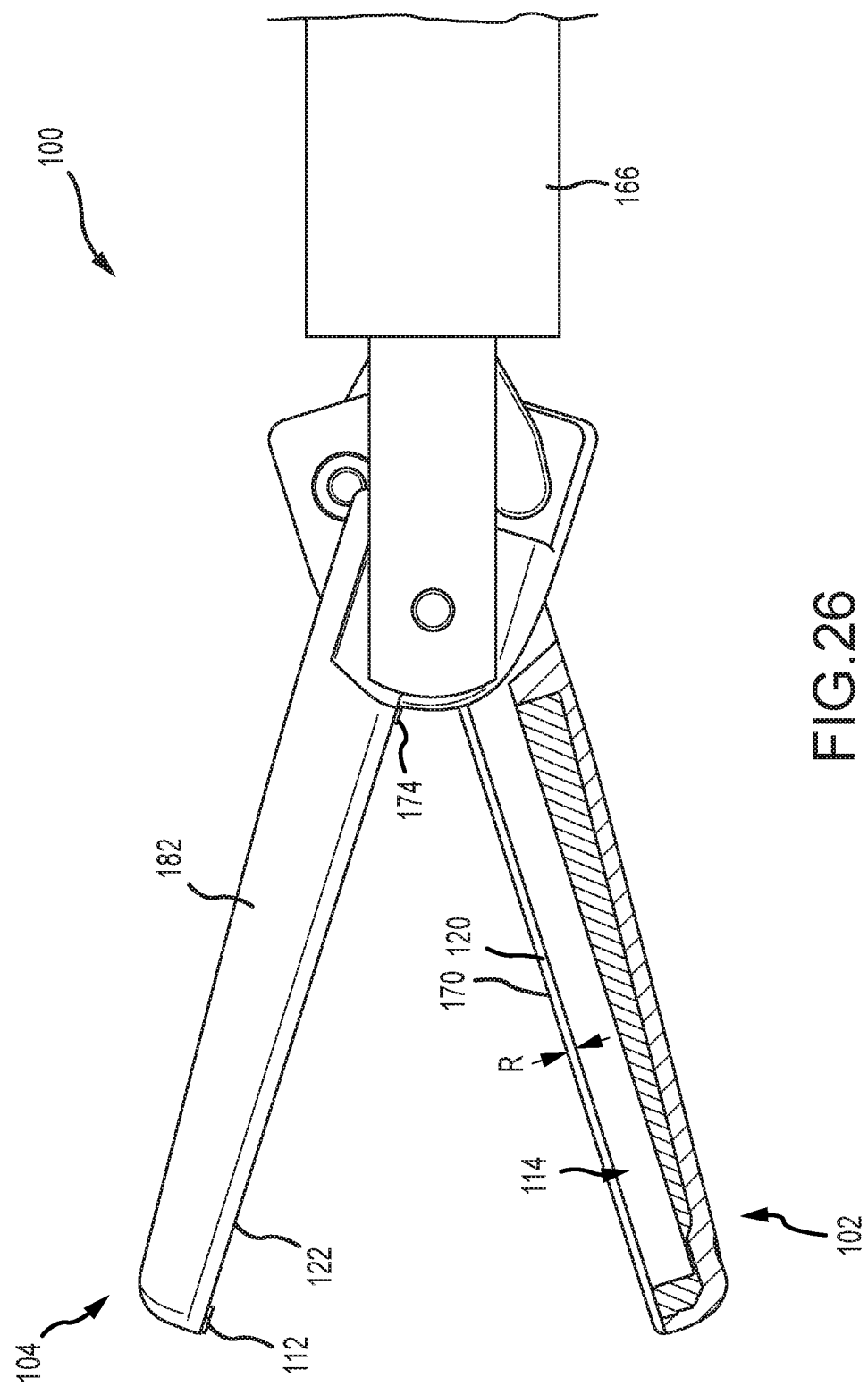

Turning now to FIGS. 25-26, an exemplary instrument 100 may include a first jaw 102 and a second jaw 104. A coating 170, 182 on the first and/or second jaws may be provided and shaped so as to expose a recessed sealing surface 120, 122. The recessed sealing surface 120, 122 may be quite narrow; for example, a distance D from the channel 114 or elongated slot may be a maximum of 0.5 millimeters in some embodiments. In some embodiments, the distance D may be more than 0.2 millimeters. In some embodiments, the distance may be no more than 0.6 millimeters. In some embodiments, the distance may be no more than 0.8 millimeters. In some embodiments, the distance D may be no more than 1 millimeter. In some embodiments, the distance D may be between 0.2 and 0.7 millimeters.

Although illustrated as a flat surface, those skilled in the art should recognize that the sealing surfaces 120, 122 in the instrument illustrated in FIG. 25 may include curvatures R1, R2, protrusions 132, and/or recesses 134 (and primary seal surface) as previously described herein with reference to the previous Figures. The instrument 100 illustrated in FIG. 25 may also have a distal travel stop 112 and/or a proximal travel stop 176 as previously described herein. Other features may be substantially as previously described herein. Of particular note, the Applicants have determined that, contrary to prior belief in the industry, an instrument such as a tissue sealer having a very narrow or thin margin of tissue contact surface results in very strong burst strengths of tissue sealed with such instruments. Moreover, because of the very small sealing surface area, the device may be held to a very low power, such as 50 Watts or less, 40 Watts or less, or 35 Watts or less, 3 Amperes or less, or 2.5 Amperes or less, or 2 Amperes or less, and still achieve strong seals, without causing damage to surrounding tissue. In some embodiments, at a power level of 50 Watts, a current of between 1.5 Amperes and 3.0 Amperes may be provided.

Figure 27:
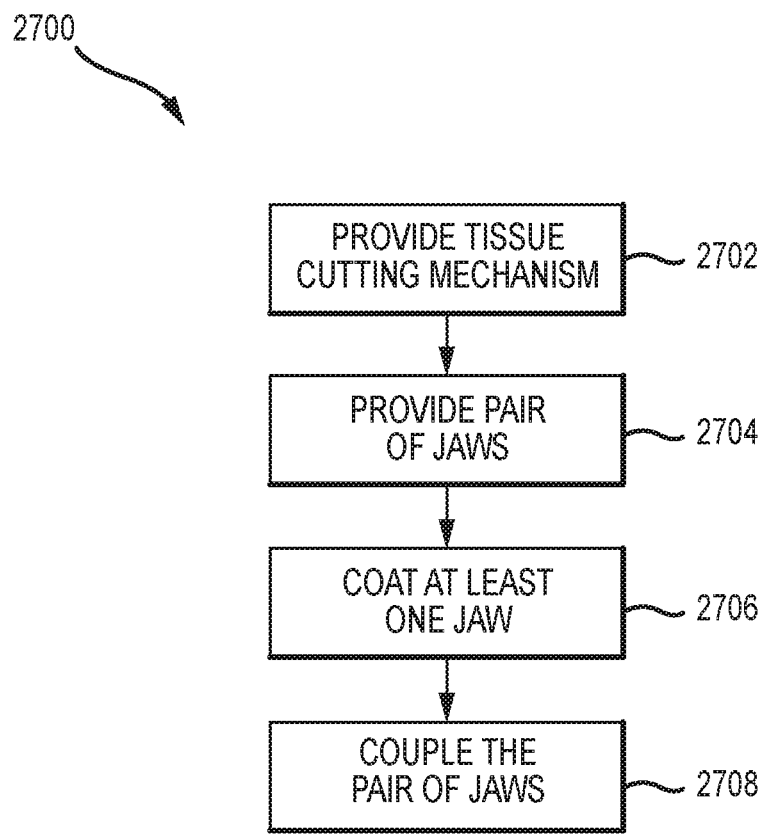

Turning now to FIG. 27, a method 2700 of making an electrosurgical instrument is described. The method 2700 may include providing 2702 a movable tissue cutting mechanism. The method 2700 may include providing 2704 a pair of jaws, at least one jaw of the pair of jaws having a conductive core member, each jaw having an elongated slot for receiving a portion of the movable tissue cutting mechanism, the cutting mechanism configured to move between a proximal position and a distal position for cutting tissue clamped between the pair of opposing jaws. The method 2700 may include coating 2706 the at least one jaw with a non-conductive coating, such that the non-conductive coating exposes a portion of the core member to form a sealing surface area recessed relative to the non-conductive coating. The method 2700 may include coupling 2708 the pair of jaws such that they oppose one another and are movable between a closed position for clamping tissue therebetween and an open position.

In some embodiments, coating 2706 comprises at least one of overmolding, plasma spraying, detonation spraying, wire arc spraying, thermal spraying, flame spraying, high velocity oxy-fuel spraying, high velocity air fuel spraying, warm spraying, or cold spraying.

The following list is a non-exhaustive list of exemplary embodiments. From the list, one skilled in the art can readily recognize that many features of the device 100 illustrated in the Figures can be added or removed, and features illustrated in a first figure may be suitable for use in a device illustrated in a second figure, even if not illustrated as such.

EXAMPLES

With reference now to Table 1, an electrosurgical instrument according to embodiments described herein was tested on 5 seals. The jaws of the instrument had a sealing surface of about 57 square millimeters, and a coating on a portion of the jaws provided for a recessed sealing surface relative to the coating. The sealing surface was recessed by at least 0.101 millimeters on each jaw, and stops provided for a gap of about 0.127 millimeters between the jaws during sealing. The device was set to nominal output settings of 50 Watts maximum power, 100 Volts maximum voltage, and 2.5 Amperes maximum current. The device was also set to cease the application of power when impedance to energy passing through the tissue reached 250 Ohms.

The device was used to apply the 5 seals listed in Table 1.

Each of the seals were cut and examined after sealing, and were determined to be of excellent quality. Specifically, the seals were found to be transparent, with a clean edge (transfer from sealed to unsealed tissue), indicating a strong seal. No damage, such as charring, was observed adjacent the seal, indicating little thermal spread.

For comparison, another device having a jaw sealing surface area of about 113 square millimeters, and the same power settings listed above (50 Watts, 100 Volts, 2.5 Amperes, and 250 Ohms stop) was tested. With all other factors being equal, the 113 square millimeter jaw was not operable to seal larger full jaw vessels. The inoperability of the 113 square millimeter jaw at the same power settings demonstrates that a smaller sealing surface area provides greater functionality at low power settings.

More specifically, a device providing a current concentration of about 0.0345 Amperes per square millimeter (or 2.00 Amperes per 58 square millimeters or less) has been proven to provide reliable sealing. In some embodiments, the device is configured to provide a current concentration of about 0.025 Amperes per square millimeter or more. In some embodiments, the device is configured to provide a current concentration of about 0.030 Amperes per square millimeter or more. In some embodiments, the device is configured to provide a current concentration of about 0.030 Amperes or more per square millimeter and a power of 50 Watts or less. Those skilled in the art will recognize that a pair of jaws 102, 104 that are not completely filled with tissue will have a higher concentration. In some embodiments, the current concentrators 132, 134 described herein may provide an effective high concentration of current to initiate a sealing action. That is, even if other areas of tissue clamped between the jaws 102, 104 do not experience a current concentration of at least 0.025 Amperes per square millimeter, the current concentrators 132, 134 may be configured to effectuate this concentration at the area near the current concentrators 132, 134, and not necessarily across all tissue clamped between the jaws 102, 104.

With reference now to FIG. 28, FIG. 29, FIG. 30, and FIG. 31 an electrosurgical instrument 100 may be substantially similar to the instrument 100 described with reference to FIG. 25. The instrument 100 may have a movable tissue cutting mechanism 106 with an elongated slot 107 therethrough. A first elongated shaft 166, which may be substantially similar to the split shaft 166 previously described herein, may house at least a proximal portion of the movable tissue cutting mechanism 106. The first elongated shaft 166 is illustrated transparently in FIG. 31 and FIG. 32 to show the relationship between the links 162, 164, the bushings, and/or the path of the cutting mechanism 106.

Figure 29:
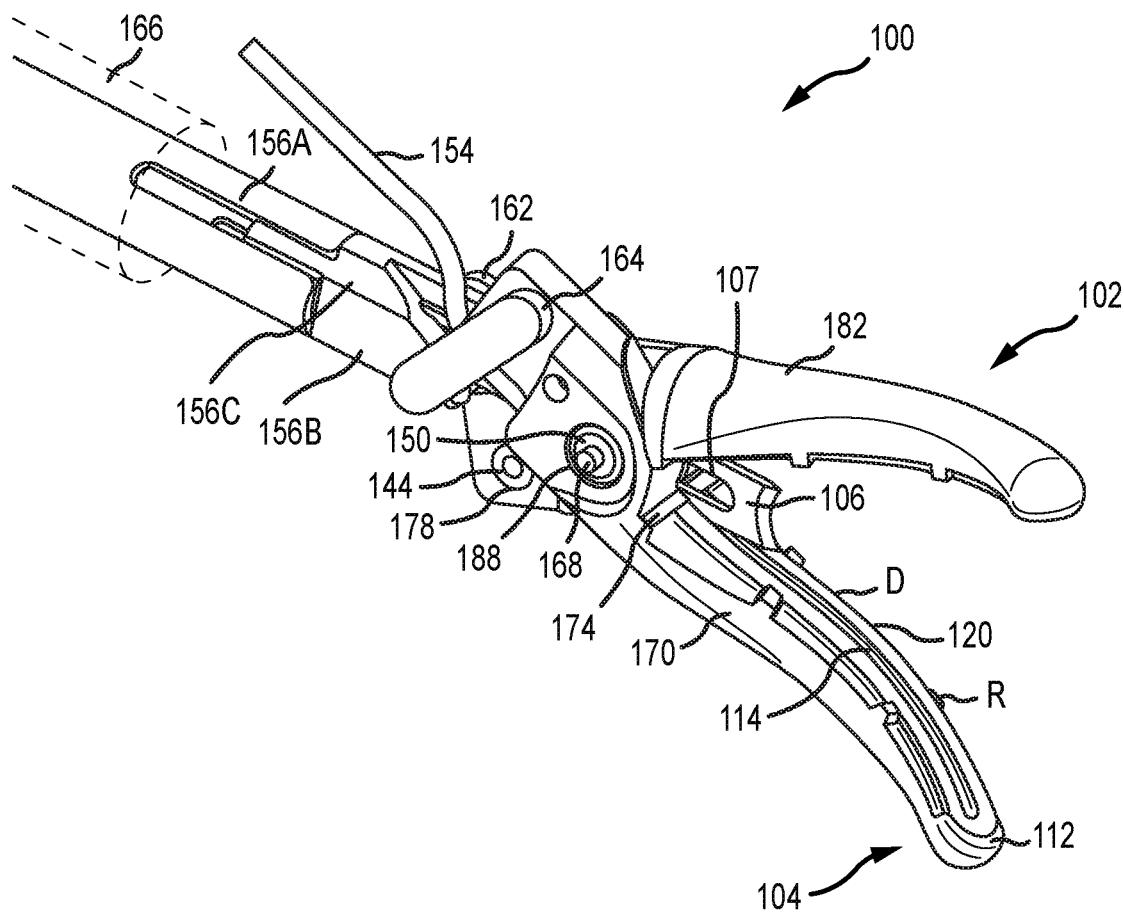
FIG. 29 is a first perspective view of an exemplary surgical instrument.
Figure 30:
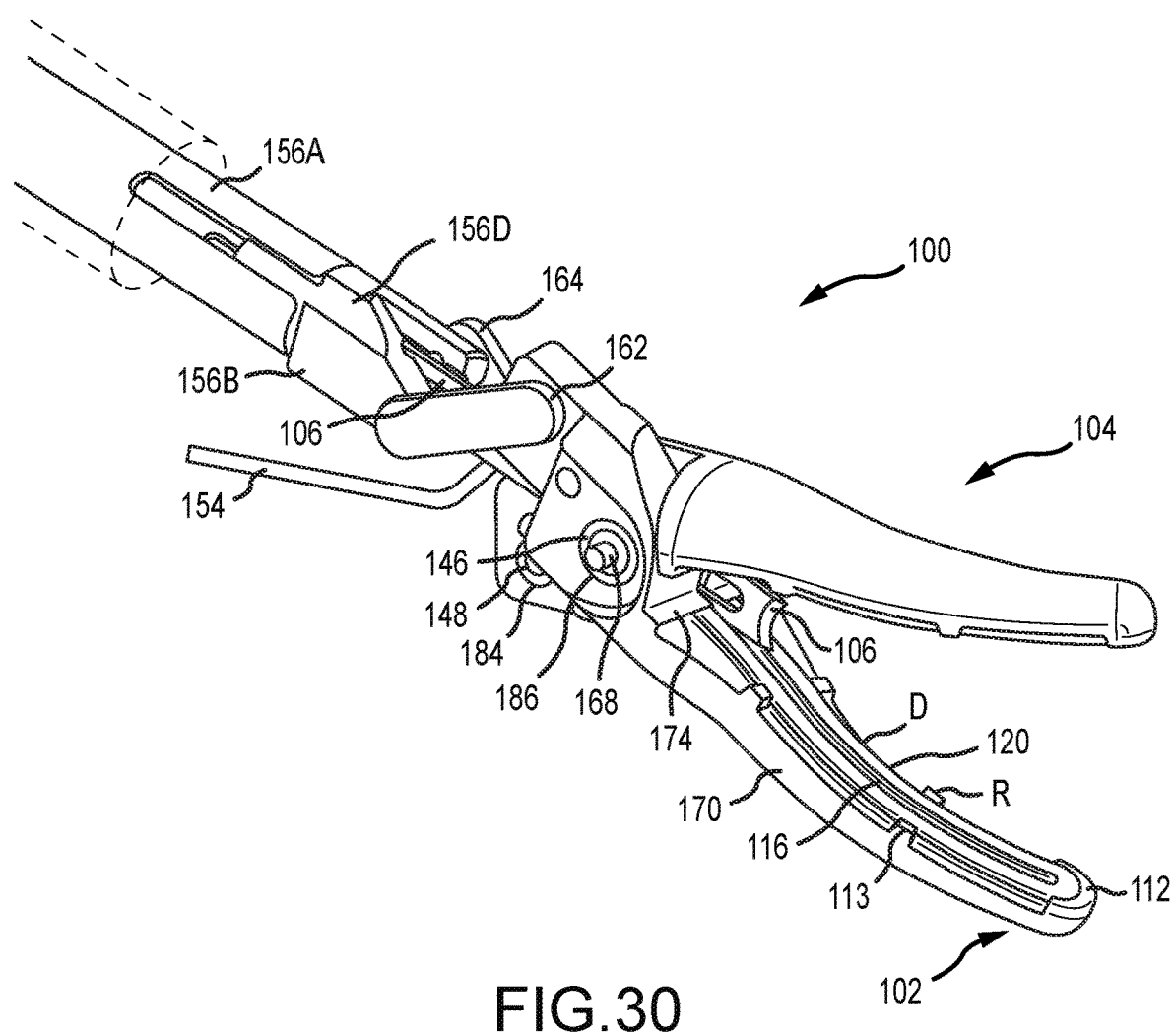
FIG. 30 is a second perspective view of the instrument in FIG. 29.
Figure 31:
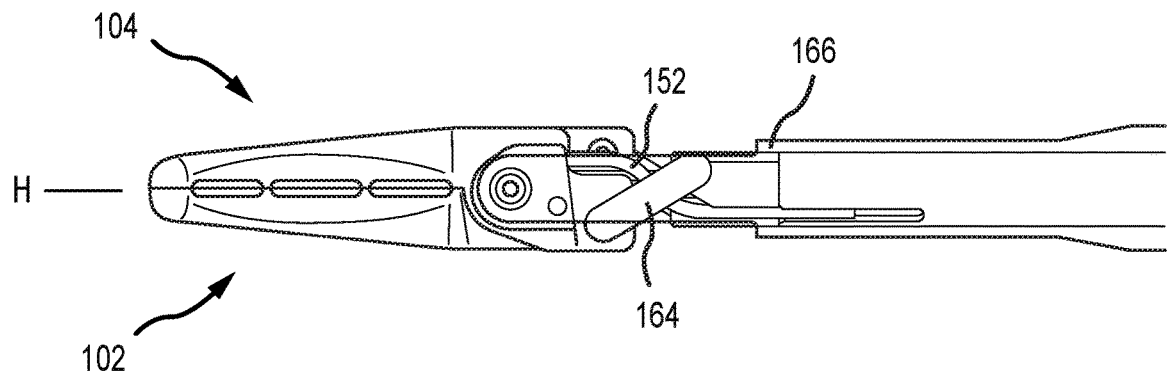
FIG. 31 is a first side view of the instrument in FIG. 29.

The instrument 100 may have a pair of opposing jaws having a first jaw 102 and a second jaw 104, the pair of opposing jaws shaped and configured to move between a closed position, as seen in FIG. 30 and FIG. 31, for clamping and sealing tissue therebetween and an open position, as seen in FIG. 28 and FIG. 29, each one of the pair of opposing jaws comprising an electrically conductive core member, an elongated slot 114, 116 for receiving the movable tissue cutting mechanism 106, and a sealing surface 120 having a sealing surface area, wherein the first jaw 102 has a first pair of non-conductive bushings 144, 146, and the second jaw 104 has a second pair of non-conductive bushings 148, 150 substantially as previously described herein.

A pin 168 may be fixed to the first elongated shaft 166 and may extend through the elongated slot 107 of the movable tissue cutting mechanism 106 and a distal one 146, 150 of the pair of non-conductive bushings in each of the jaws. As arranged, the pair of opposing jaws 102, 104 is rotatable relative to the first elongated shaft 166, and the movable tissue cutting mechanism 106 is slidable relative to the first elongated shaft 166.

Continuing with FIGS. 28-31, links 162, 164 having distal ends rotatably coupled to proximal ones 144, 148 of the pairs of non-conductive bushings 144, 146, 148, 150 in each of the jaws. Proximal ends of the links 162, 164 may be rotatably coupled to a second elongated shaft 156A, the second elongated shaft 156A interior of and translatable relative the first elongated shaft 166. The second elongated shaft 156A may also be referenced herein as a split rod 156 (see also FIG. 9). In some embodiments, the links 162, 164 may be coupled to the second elongated shaft 156A at a distal portion 156B coupled to or unitary with the second elongated shaft 156A. In some embodiments, the distal portion 156B coupled to or unitary with the second elongated shaft 156A may include a recess or groove 156C for seating a portion of a coated wire 154 to a jaw 104. Another groove 156D may seat another cable (not illustrated for clarity) to another jaw 102. In some embodiments, the cutting mechanism 106 may pass through a slot in the distal portion 156B and/or may pass through a central portion of the second elongated shaft 156A or split rod 156. The distal portion 156B may be press fit to, welded to, and/or otherwise bonded to the proximal portion 156A. The distal portion 156B may be unitary with the proximal portion 156A. The proximal portion 156A may have a groove or slot for receiving a portion of the conductive wire 152, 154, see e.g. FIG. 31. The wire 152, 154 may be routed exterior of the distal portion 156B and interior of the proximal portion 156A in some embodiments. A distal portion of the wire 152, 154 may be exterior of the distal portion 156B and a proximal portion of the wire 152, 154 may be interior of the proximal portion 156A. That is, the wire 152, 154 may be routed through the links 162, 164 past the distal portion 156B and into a slot 156C, 156D.

As previously described each bushing of the first pair of non-conductive bushings and the second pair of non-conductive bushings may comprise a ceramic.

The sealing surface area of each jaw may extend a distance of no more than 0.8 millimeters from the respective elongated slot.

In some embodiments, the sealing surface area extends a distance of between 0.2 millimeters and 0.7 millimeters from the elongated slot.

In some embodiments, each core member of the pair of opposing jaws is partially coated with a coating 170 having a substantially non-conductive material, and a portion of each core member is exposed to form the sealing surface of the respective each jaw thereon. The coating may be applied by at least one of overmolding, plasma spraying, detonation spraying, wire arc spraying, thermal spraying, flame spraying, high velocity oxy-fuel spraying, high velocity air fuel spraying, warm spraying, or cold spraying. The coating 170 may provide a travel stop 174, 112, 113 to maintain a gap between the pair of jaws when in the closed position. The gap may be 0.18 millimeters or less. In some embodiments, the gap is at least 0.07 millimeters. In some embodiments, a proximal portion of the gap is four times greater than a distal portion of the gap or more.

Each core member may be coupled to an electrically conductive wire 152, 154, which may be coated, by at least one of soldering, welding, an insulation-displacement contact, or an insulation piercing contact. The figures illustrate one wire 154 in an expanded or non-assembled state for clarity, while the other wire 152 is not illustrated, to show other features of the device 100.

As previously described herein, the device 100 may be further configured to deliver a maximum power of 50 Watts and a maximum current of 3 Amperes to tissue clamped between the jaws 102, 104. The pair of jaws may be further shaped to fit through a cannula having an inner diameter of 6 millimeters or less when the jaws are in the closed position. The elongated slots may have a non-linear shape.

The non-conductive bushings isolate the links and the pin from the core members.

In some embodiments, the sealing surface area of each jaw 102, 104 may be less than 24 square millimeters; and the sealing surface area of each jaw extends no more than 0.8 millimeters from the elongated slot of the respective jaw.

As illustrated, the travel stops may be positioned adjacent the sealing surfaces.

In some embodiments, the travel stops comprise a ceramic.

In some embodiments, the travel stops comprise an overmold or spray coating.

Each bushing of the first and second pairs of bushings may act as a heat sink and provide electrical isolation in some embodiments, and/or at least one bushing of the first pair of non-conductive bushings and the second pair of non-conductive bushings may include at least one of a non-compressible material or a low compression material.

In some embodiments, at least one bushing of the first pair of non-conductive bushings and the second pair of non-conductive bushings has a thermoplastic polymer. In some embodiments, the bushings include a metal with an isolating surface treatment.

Figure 32:
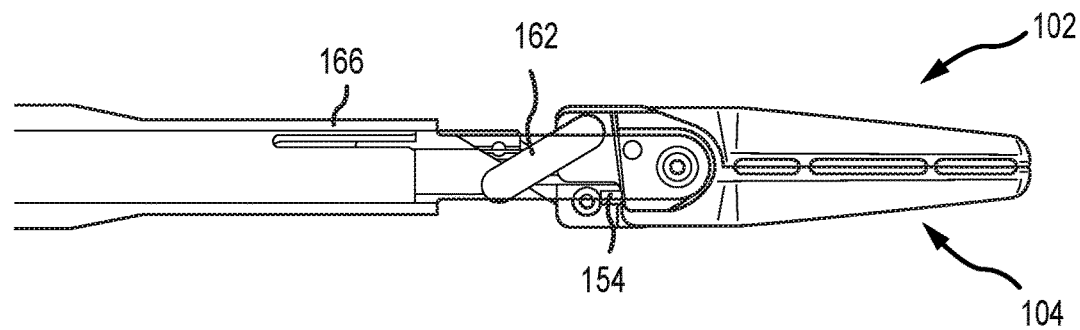
FIG. 32 is a second side view of the instrument in FIG. 29.

As illustrated most clearly in FIG. 30 and FIG. 31, in some embodiments, the path of travel cutting mechanism 106 defines a horizontal direction, see FIG. 29 and FIG. 30, and one bushing of the first pair of bushings 144, 146 and/or one bushing of the second pair of bushings 148, 150 is not in line with the path of travel of the cutting mechanism 106. In some embodiments, a distal one 146, 150 of the pairs of bushings may be in line with the path of travel of the cutting mechanism. The links 162, 164 may be elongated and coupled to the distal portion 156B and proximal ones 144, 148 of the bushings 144, 146, 148, 150. The elongated direction of the links 162, 164 may not be parallel to the horizontal direction defined by the travel path of the cutting mechanism 106, as illustrated in FIG. 31 and FIG. 32, when the jaws 102, 104 are in the closed position. In some embodiments, the links 162, 164 may have a portion that is above the horizontal H defined by the travel path of the cutting mechanism 106 and a portion that is below the horizontal H, as illustrated in FIG. 31 and FIG. 32. In some embodiments, the bushings 144, 146, 148, 150 may not be equidistant from the travel path or cutting mechanism 106 when the jaws 102, 104 are in the closed position. In some embodiments, one or both links 162, 164 have a width and an elongated length, and when the pair of jaws 102, 104 are in the closed position, the elongated length is not parallel to a horizontal H defined by a travel direction of the cutting mechanism 106. The length of the links 162, 164 may be greater than the width.

The following is a non-exhaustive list of embodiments described herein.

Embodiment 1. An electrosurgical instrument comprising: a movable tissue cutting mechanism; and a pair of opposing jaws having a first jaw and a second jaw, the pair of opposing jaws shaped and configured to move between a closed position for clamping and sealing tissue therebetween and an open position; wherein at least one jaw comprises a conductive core member and a non-conductive coating, the non-conductive coating covering a portion of the core member and exposing a portion of the core member to form a sealing surface area recessed relative to the non-conductive coating; and each jaw comprises an elongated slot for receiving a portion of the cutting mechanism, the cutting mechanism configured to move between a proximal position and a distal position for cutting tissue clamped between the pair of opposing jaws.

Embodiment 2. The instrument of embodiment 1, wherein: the non-conductive coating is formed on the core member of the at least one jaw by at least one of an overmold, a plasma spray coating, a detonation spray coating, a wire arc spray coating, a thermal spray coating, a flame spray coating, a high velocity oxy-fuel spray coating, a high velocity air fuel coating, a warm spray coating, or a cold spray coating.

Embodiment 3. The instrument of embodiment 1 or 2, wherein: the sealing surface area of the at least one jaw extends a distance of no more than 0.8 millimeters from the elongated slot.

Embodiment 4. The instrument of any one of embodiment 1-3, wherein: the sealing surface area extends a distance of between 0.2 millimeters and 0.7 millimeters from the elongated slot.

Embodiment 5. The instrument of any one of embodiments 1-4, wherein: the sealing surface area of the at least one jaw extends no more than 0.6 millimeters from the elongated slot.

Embodiment 6. The instrument of any one of embodiments 1-5, wherein: the coating is configured to maintain a gap between the surface areas of the pair of jaws in the closed position; and the gap is 0.05 millimeters or more.

Embodiment 7. The instrument of embodiment 6, wherein: the gap is 0.18 millimeters or less.

Embodiment 8. The instrument of embodiment 7, wherein: the gap is at least 0.07 millimeters.

Embodiment 9. The instrument of any one of embodiments 1-8, wherein: the non-conductive coating is formed on the core member by at least one of an overmold, a plasma spray coating, a detonation spray coating, a wire arc spray coating, a thermal spray coating, a flame spray coating, a high velocity oxy-fuel spray coating, a high velocity air fuel coating, a warm spray coating, or a cold spray coating.

Embodiment 10. The instrument of embodiment 9, wherein: the device is further configured to deliver a maximum power of 50 Watts and a maximum current of 3 Amperes to tissue clamped between the jaws.

Embodiment 11. The instrument of any one of embodiments 1-10, wherein: the pair of jaws are further shaped to fit through a cannula having an inner diameter of 6 millimeters or less when the jaws are in the closed position.

Embodiment 12. The instrument of any one of embodiments 1-11, further comprising: a linkage mechanism for controlling relative rotation of the pair of jaws, the linkage mechanism having a first pair of non-conductive bushings in the first jaw, a second pair of non-conductive bushings in the second jaw, a pin extending through a first one of the bushings in each of the jaws to enable rotation relative to a split rod, and a link coupled to a second one of the bushings in each of the jaws.

Embodiment 13. The instrument of embodiment 12, wherein: the non-conductive bushings isolate the links and the pin from the core members.

Embodiment 14. The instrument of any one of embodiments 1-13, wherein: the sealing surface area of the at least one jaw is less than 24 square millimeters; and the sealing surface area extends no more than 0.8 millimeters from the elongated slot.

Embodiment 15. The instrument of any one of embodiments 1-14, wherein: at least one of (a) the sealing surface area of the at least one jaw is less than 10 square millimeters or (b) the sealing surface area extends no more than 0.6 millimeters from the elongated slot.

Embodiment 16. The instrument of any one of embodiments 1-15, wherein: the instrument is further configured to apply no more than 50 Watts of power to tissue clamped between the opposing jaws; and the instrument is further configured to apply no more than 3 Amperes of current to tissue clamped between the opposing jaws.

Embodiment 17. The instrument of any one of embodiments 1-16, wherein: the least one jaw has a proximal end having a pair of non-conductive bushings, and a distal end; the coating is configured to maintain a gap between the sealing surfaces of the pair of jaws; and a proximal portion of the gap is greater than a distal portion of the gap.

Embodiment 18. The instrument of embodiment 17, wherein: the coating extends from the proximal region to the distal region.

Embodiment 19. The instrument of any one of embodiments 1-18, wherein: the recessed sealing surface of the at least one jaw comprises a primary sealing surface; and the primary sealing surface is a curved surface.

Embodiment 20. The instrument of embodiment 19; wherein: the recessed sealing surface further comprises at least one of a protrusion or a recess for concentrating a current flow from the at least one jaw through tissue clamped between the pair of jaws.

Embodiment 21. The instrument of any one of the preceding embodiments, wherein: the recessed sealing surface of the at least one jaw comprises a primary sealing surface; and the primary sealing surface is a flat surface.

Embodiment 22. The instrument of embodiment 21 wherein: the recessed sealing surface of the at least one jaw further comprises at least one of a protrusion or a recess for concentrating a current flow from the at least one jaw through tissue clamped between the pair of jaws.

Embodiment 23. The instrument of any one of the preceding embodiments, wherein: the recessed sealing surface of the at least one jaw comprises a primary sealing surface and at least one of a protrusion or a recess for concentrating a current flow from the at least one jaw through tissue clamped between the pair of jaws.

Embodiment 24. The instrument of any one of the preceding embodiments, wherein: the recessed sealing surface of the at least one jaw comprises a protrusion; the other one of the pair of opposing jaws comprises a recess opposing the protrusion; and wherein the protrusion and the recess are configured to concentrate a current flow through the protrusion and the recess.

Embodiment 25. The instrument of any one of embodiments 1-24, wherein: at least a portion of the elongated slot is non-linear.

Embodiment 26. A method of making an electrosurgical instrument, comprising: providing a movable tissue cutting mechanism; providing a pair of jaws, at least one jaw of the pair of jaws having a conductive core member, each jaw having an elongated slot for receiving a portion of the movable tissue cutting mechanism, the cutting mechanism configured to move between a proximal position and a distal position for cutting tissue clamped between the pair of opposing jaws; coating the at least one jaw with a non-conductive coating, such that the non-conductive coating exposes a portion of the core member to form a sealing surface area recessed relative to the non-conductive coating; coupling the pair of jaws such that they oppose one another and are movable between a closed position for clamping tissue therebetween and an open position.

Embodiment 27. The method of embodiment 26, wherein: coating comprises at least one of overmolding, plasma spraying, detonation spraying, wire arc spraying, thermal spraying, flame spraying, high velocity oxy-fuel spraying, high velocity air fuel spraying, warm spraying, or cold spraying.

Embodiment 28. An electrosurgical instrument comprising: a movable tissue cutting mechanism; and a pair of opposing jaws having a first jaw and a second jaw, the pair of opposing jaws shaped and configured to move between a closed position for clamping and sealing tissue clamped therebetween and an open position; wherein the first jaw comprises an exposed tissue sealing surface, the exposed tissue sealing surface having a primary sealing surface and least one protrusion extending from the primary sealing surface for concentrating a sealing current through the at least one protrusion; the second jaw comprises an exposed tissue sealing surface, the exposed tissue sealing surface having a primary sealing surface and at least one recess in the primary sealing surface for concentrating a sealing current through the at least one recess; wherein the at least one protrusion and the at least one recess oppose one another when the pair of opposing jaws are in the closed position; and each one of the pair of opposing jaws comprises an elongated slot for receiving a portion of the cutting mechanism, the cutting mechanism configured to move between a proximal position and a distal position for cutting tissue clamped between the pair of opposing jaws.

Embodiment 29. The instrument of embodiment 28, wherein: at least one of the first jaw or the second jaw has a conductive core member and a non-conductive coating, the non-conductive coating covering a portion of the conductive core member and exposing the tissue sealing surface such that the tissue sealing surface is recessed relative to the non-conductive coating; and the non-conductive coating is formed on the core member of the at least one jaw by at least one of an overmold, a plasma spray coating, a detonation spray coating, a wire arc spray coating, a thermal spray coating, a flame spray coating, a high velocity oxy-fuel spray coating, a high velocity air fuel coating, a warm spray coating, or a cold spray coating.

Embodiment 30. The instrument of embodiment 28 or 29, wherein: at least one of the first jaw or the second jaw comprises at least one of a non-conductive distal travel stop, the distal travel stop positioned distal of the elongated slot and configured to maintain a gap between the primary sealing surfaces of the first and second jaws in the closed position; or a non-conductive proximal travel stop, the proximal travel stop positioned proximal of the exposed tissue sealing surface and configured to maintain a gap between the primary seal surfaces of the first and second jaws in the closed position; and wherein the gap is between 0.05 millimeters and 0.18 millimeters.

Embodiment 31. The instrument of any one of embodiments 28-30, wherein: the instrument is configured to maintain a gap between the at least one protrusion and the at least one recess when the jaws are in the closed position, wherein the gap is between 0.05 millimeters and 0.18 millimeters.

Embodiment 32. The instrument of any one of embodiments 28-31, wherein: the device is further configured to deliver a maximum power of 50 Watts to tissue clamped between the jaws.

Embodiment 33. The instrument of any one of embodiment 28-32, wherein: the instrument is further shaped to fit through a cannula having an inner diameter of 6 millimeters or less when the jaws are in the closed position.

Embodiment 34. The instrument of any one of embodiments 28-33, further comprising: a linkage mechanism for controlling relative rotation of the pair of jaws, the linkage mechanism having a first pair of non-conductive bushings in the first jaw, a second pair of non-conductive bushings in the second jaw, a pin extending through a first one of the bushings in each of the jaws to enable rotation relative to a split rod, and a link coupled to a second one of the bushings in each of the jaws.

Embodiment 35. The instrument of embodiment 34, wherein: the non-conductive bushings isolate the links and the pin from core members of the pair of jaws.

Embodiment 36. The instrument of any one of embodiments 28-35, wherein: the exposed tissue sealing surface at least one of the first or second jaws has a surface area of 24 square millimeters or less.

Embodiment 37. The instrument of embodiment 36, wherein: the exposed tissue sealing surface of the at least one of the first or second jaws has a surface area of 10 square millimeters or less.

Embodiment 38. The instrument of any one of embodiments 28-37, wherein: the instrument is further configured to apply no more than 50 Watts of power and no more than 3 Amperes to tissue clamped between the pair of opposing jaws.

Embodiment 39. The instrument of any one of embodiments 28-38, wherein: at least one of the first or second jaw has a conductive core member with a proximal end and a distal end; the proximal end of the core member has a pair of recesses; and a pair of non-conductive bushings are positioned in the pair of recesses.

Embodiment 40. The instrument of any one of embodiments 28-39, wherein: the primary sealing surfaces of the first and second jaws are curved.

Embodiment 41. The instrument of embodiment 40, wherein: a first one of the primary sealing surfaces is concave; and a second one of the primary sealing surfaces is convex.

Embodiment 42. The instrument of embodiment 41, wherein: a first one of the primary sealing surfaces is concave; and a second one of the primary sealing surfaces is convex; whereby the primary sealing surfaces are shaped to promote disengagement of tissue sealed therebetween upon moving from the closed position to the open position.

Embodiment 43. The instrument of any one of embodiments 28-42, wherein: at least a portion of the elongated slot is non-linear.

Embodiment 44. A method of making an electrosurgical instrument, comprising: providing a movable tissue cutting mechanism; providing a pair of jaws having a first jaw and a second jaw, each of the jaws having an elongated slot for receiving the movable tissue cutting mechanism, the first jaw having an exposed tissue sealing surface, the exposed tissue sealing surface having a primary sealing surface and least one protrusion extending from the primary sealing surface for concentrating a sealing current through the at least one protrusion, the second jaw having an exposed tissue sealing surface, the exposed tissue sealing surface having a primary sealing surface and at least one recess in the primary sealing surface for concentrating a sealing current through the at least one recess; shaping the pair of jaws such that the at least one protrusion and the at least one recess oppose one another when the pair of opposing jaws are in the closed position; coupling the pair of jaws such that they oppose one another and are movable between a closed position for clamping tissue therebetween and an open position.

Embodiment 45. The method of embodiment 44, further comprising: shaping one of the primary sealing surfaces with a concave curvature; and shaping the other one of the primary sealing surfaces with a convex curvature.

Embodiment 46. Any one of the preceding embodiments, wherein the instrument is a vessel sealing and cutting instrument.

Embodiment 47. Any one of the preceding embodiments, wherein each jaw has a jaw sealing surface, the jaw sealing surface having a surface area of between 23 square millimeters and 58 square millimeters, and the device is configured to apply no more than 50 Watts of power with no more than 3 Amperes and no more than 100 volts to tissue clamped between the jaws, the tissue being a vessel that is greater than 5 millimeters wide and up to 15 millimeters wide, and wherein the device is configured to seal the tissue clamped between the jaws within 5 seconds or less.

Embodiment 48. The device of embodiment 47, wherein the device is configured to seal the tissue clamped between the jaws within 4 seconds or less.

Embodiment 49. The device of embodiments 47 or 48, wherein the device is configured to deliver no more than 3 Amperes to the tissue clamped between the jaws.

Embodiment 50. The device or method of any one of the preceding embodiments, wherein the device is configured to apply a current concentration of at least 0.025 Amperes per square millimeter across at least a portion of tissue clamped between the jaws.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "fastener" should be understood to encompass disclosure of the act of "fastening"—whether explicitly discussed or not—and, conversely, were there only disclosure of the act of "fastening", such a disclosure should be understood to encompass disclosure of a "fastening mechanism". Such changes and alternative terms are to be understood to be explicitly included in the description.

Moreover, the claims shall be construed such that a claim that recites "at least one of A, B, or C" shall read on a device that requires "A" only. The claim shall also read on a device that requires "B" only. The claim shall also read on a device that requires "C" only. Similarly, the claim shall also read on a device that requires "A+B", and so forth. The claim shall also read on a device that requires "A+B+C".

The claims shall also be construed such that any relational language (e.g. perpendicular, straight, parallel, flat, etc.) is understood to include the recitation "within a reasonable manufacturing tolerance at the time the device is manufactured or at the time of the invention, whichever manufacturing tolerance is greater".

In conclusion, the present invention provides, among other things, a system and method for an electrosurgical procedure. Those skilled in the art can readily recognize that numerous variations and substitutions may be made in the invention, its use and its configuration to achieve substantially the same results as achieved by the embodiments described herein.

Accordingly, there is no intention to limit the invention to the disclosed exemplary forms. Many variations, modifications and alternative constructions fall within the scope and spirit of the disclosed invention as expressed in the claims.

What is claimed is:

1. An electrosurgical instrument comprising:
a movable tissue cutting mechanism;
a shaft housing at least a proximal portion of the movable tissue cutting mechanism;
a pair of opposing jaws having a first jaw and a second jaw, the pair of opposing jaws shaped and configured to move between a closed position for clamping and sealing tissue therebetween and an open position, each one of the pair of opposing jaws comprising an electrically conductive core member, an elongated slot for receiving the movable tissue cutting mechanism, and a sealing surface having a sealing surface area, wherein the first jaw has a first pair of non-conductive bushings, and the second jaw has a second pair of non-conductive bushings, and wherein the conductive core member of each one of the jaws further shaped to receive the non-conductive bushings;
a pin coupled to the shaft and a distal pair of non-conductive bushings in the jaws, wherein the pin passes through the distal pair of non-conductive bushings and the cutting mechanism, and wherein each one of the pair of opposing jaws is rotatable relative to the shaft, and wherein the movable tissue cutting mechanism is slidable relative to the shaft;
a conductive medium operatively coupled to the conductive core member; and
a first link having a distal end rotatably coupled to a proximal one of the pair of non-conductive bushings in the first jaw and a proximal end rotatably coupled to a rod, the rod interior of and translatable relative to the shaft; and
wherein the first jaw further has a coating made of a substantially non-conductive material covering a substantial portion of the conductive core member but exposing the seal surface, whereby the first pair of non-conductive bushings and the coating are configured to substantially isolate the conductive core member and limit an energy path from the conductive medium to the seal surface of the first jaw; and
wherein the second jaw further has a coating made of a substantially non-conductive material covering a substantial portion of the conductive core member but exposing the seal surface, whereby the second pair of non-conductive bushings and the coating are configured to substantially isolate the conductive core member and limit an energy path from the conductive medium to the seal surface of the second jaw.

2. The instrument of claim 1, wherein:
each bushing of the first pair of non-conductive bushings and the second pair of non-conductive bushings comprises a ceramic.

3. The instrument of claim 1 wherein:
the sealing surface area of each jaw extends a distance of no more than 0.8 millimeters outwardly from the periphery of the respective elongated slot.

4. The instrument of claim 3, wherein:
the sealing surface area extends a distance of between 0.2 millimeters and 0.7 millimeters outwardly from the periphery of the elongated slot.

5. The instrument of claim 1, wherein:
the pair of opposing jaws is configured to have a gap between the pair of jaws when in the closed position; and wherein
the gap is between 0.05 millimeters and 0.18 millimeters.

6. The instrument of claim 5, wherein:
the gap is between 0.05 millimeters and 0.07 millimeters.

7. The instrument of claim 1, wherein:
the instrument is further configured to deliver a maximum power of 50 Watts and a maximum current of 3 Amperes to tissue clamped between the jaws.

8. The instrument of claim 1, wherein:
the pair of jaws are further shaped to fit through a cannula having an inner diameter of 6 millimeters or less when the jaws are in the closed position; and wherein the elongated slot comprises a non-linear shape.

9. The instrument of claim 1, wherein:
the first pair of non-conductive bushings isolate the first link and the pin from the core member of the first jaw; and
the second pair of non-conductive bushings isolate the second link and the pin from the core member of the second jaw.

10. The instrument of claim 5, wherein:
a proximal portion of the gap is greater than a distal portion of the gap.

11. The instrument of claim 5, further comprising:
one or more travel stops to maintain the gap, the one or more travel stops adjacent the sealing surface areas.

12. The instrument of claim 5, further comprising:
one or more travel stops to maintain the gap, the one or more travel stops comprising an overmold or spray coating.

13. The instrument of claim 1, wherein:
at least one bushing of the first pair of non-conductive bushings and the second pair of non-conductive bushings comprise at least one of a non-compressible material or a low compression material.

14. The instrument claim 1, wherein:
the cutting mechanism further comprises an elongated aperture therethrough; and
the pin further passes through the elongated aperture of the cutting mechanism.

15. The instrument claim 1, wherein:
the cutting mechanism further comprises an elongated aperture therethrough;
the pin further passes through the elongated aperture of the cutting mechanism;
the pair of opposing jaws is configured to have a gap between the pair of jaws when in the closed position; and wherein
the gap is between 0.05 millimeters and 0.18 millimeters.

16. The instrument claim 1, wherein:
the cutting mechanism further comprises an elongated aperture therethrough;
the pin further passes through the elongated aperture of the cutting mechanism; and
the instrument is further configured to deliver a maximum power of 50 Watts and a maximum current of 3 Amperes to tissue clamped between the jaws.

17. The instrument claim 1, wherein:
the cutting mechanism further comprises an elongated aperture therethrough;
the pin further passes through the elongated aperture of the cutting mechanism;
the instrument is further configured to deliver a maximum power of 50 Watts and a maximum current of 3 Amperes to tissue clamped between the jaws;
the pair of jaws are further shaped to fit through a cannula having an inner diameter of 6 millimeters or less when the jaws are in the closed position; and
wherein the elongated slot comprises a non-linear shape.

18. The instrument of claim 1, wherein:
the cutting mechanism further comprises an elongated aperture therethrough;
the pin further passes through the elongated aperture of the cutting mechanism; wherein
each bushing of the first pair of non-conductive bushings is configured to isolate the first link and the pin from the conductive core member of the first jaw; and wherein
each bushing of the second pair of non-conductive bushings is configured to isolate the second link and the pin from the conductive core member of the second jaw.

* * * * *